US010182868B2

(12) United States Patent
Meier et al.

(10) Patent No.: US 10,182,868 B2
(45) Date of Patent: Jan. 22, 2019

(54) APPARATUS AND METHODS FOR USING AN ELECTROMAGNETIC TRANSPONDER IN ORTHOPEDIC PROCEDURES

(71) Applicant: VARIAN MEDICAL SYSTEMS, INC., Palo Alto, CA (US)

(72) Inventors: Eric Meier, Bellevue, WA (US); Steven C. Dimmer, Bellevue, WA (US); J. Nelson Wright, Mercer Island, WA (US); Rich Edelson, Portland, OR (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 0 days.

(21) Appl. No.: 14/243,825

(22) Filed: Apr. 2, 2014

(65) Prior Publication Data

US 2014/0303489 A1    Oct. 9, 2014

Related U.S. Application Data

(62) Division of application No. 12/159,554, filed as application No. PCT/US2006/044767 on Nov. 17, 2006.

(Continued)

(51) Int. Cl.
*A61B 90/00* (2016.01)
*A61B 5/00* (2006.01)
(Continued)

(52) U.S. Cl.
CPC ............ *A61B 19/54* (2013.01); *A61B 5/0002* (2013.01); *A61B 5/062* (2013.01); *A61B 5/686* (2013.01);
(Continued)

(58) Field of Classification Search
None
See application file for complete search history.

(56) References Cited

U.S. PATENT DOCUMENTS 3,967,161 A   6/1976 Lichtblau
4,023,167 A   5/1977 Wahlstrom
(Continued)

FOREIGN PATENT DOCUMENTS

CN        17788688 A    6/2006
WO        WO96/03925    2/1996
(Continued)

OTHER PUBLICATIONS

International Search Report and Written Opinion issued in PCT/US2006/044767 and dated Jun. 12, 2008, 8 pages.

*Primary Examiner* — Leslie Lopez
(74) *Attorney, Agent, or Firm* — Perkins Coie LLP

(57) ABSTRACT

Electromagnetic transponders as markers are used to localize and guide orthopedic procedures including: knee replacement, hip replacement, shoulder replacement, damaged bone reconstruction, and spine surgery, and more particularly, to guide orthopedic surgical navigation and alignment techniques and instruments. For example, the marker could further be used in any number of guides or templates that attach to the bony anatomy; such as a surgical guide, cutting guide, cutting jig, resection block and/or resurfacing guide. Further, the marker could be incorporated into an existing intramedullary guide rod for a femur and an extramedullary guide rod for a tibia in a knee replacement surgery; or into an external surgical guide system, or the marker could eliminate the need for an external template altogether. According to yet another anticipated use of the tracking system, the marker could be used in conjunction with or replace an optical alignment system.

9 Claims, 18 Drawing Sheets

Related U.S. Application Data

(60) Provisional application No. 60/737,907, filed on Nov. 17, 2005.

(51) Int. Cl.

| | | |
|---|---|---|
| *A61F 2/44* | (2006.01) | |
| *A61B 19/00* | (2006.01) | |
| *A61B 5/06* | (2006.01) | |
| *A61B 17/32* | (2006.01) | |
| *G06F 19/00* | (2018.01) | |
| *A61B 17/15* | (2006.01) | |
| *A61B 17/17* | (2006.01) | |
| *A61F 2/32* | (2006.01) | |
| *A61F 2/38* | (2006.01) | |
| *A61F 2/30* | (2006.01) | |

(52) U.S. Cl.
CPC .............. *A61B 17/32* (2013.01); *A61B 90/39* (2016.02); *G06F 19/00* (2013.01); *A61B 5/4504* (2013.01); *A61B 17/15* (2013.01); *A61B 17/155* (2013.01); *A61B 17/157* (2013.01); *A61B 17/17* (2013.01); *A61B 17/1757* (2013.01); *A61B 2017/320052* (2013.01); *A61B 2090/3958* (2016.02); *A61B 2090/3966* (2016.02); *A61B 2090/3975* (2016.02); *A61B 2090/3991* (2016.02); *A61F 2/32* (2013.01); *A61F 2/38* (2013.01); *A61F 2/441* (2013.01); *A61F 2002/3067* (2013.01); *A61F 2250/0002* (2013.01)

(56) References Cited

U.S. PATENT DOCUMENTS

| | | |
|---|---|---|
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson, III et al. |
| 4,643,196 A | 2/1987 | Tanaka et al. |
| 4,653,496 A | 3/1987 | Bundy et al. |
| 4,696,287 A | 9/1987 | Hortmann et al. |
| 4,795,995 A | 1/1989 | Eccleston et al. |
| 4,799,495 A | 1/1989 | Hawkins et al. |
| 4,909,789 A | 3/1990 | Taguchi et al. |
| 4,936,823 A | 6/1990 | Colvin et al. |
| 4,945,914 A | 8/1990 | Allen |
| 4,994,079 A | 2/1991 | Genese et al. |
| 5,031,634 A | 7/1991 | Simon |
| 5,062,847 A | 11/1991 | Barnes |
| 5,095,224 A | 3/1992 | Renger |
| 5,099,845 A | 3/1992 | Besz et al. |
| 5,107,862 A | 4/1992 | Fabian |
| 5,142,292 A | 8/1992 | Chang |
| 5,170,055 A | 12/1992 | Carroll et al. |
| 5,325,873 A | 7/1994 | Hirschi et al. |
| 5,353,804 A | 10/1994 | Kornberg et al. |
| 5,409,004 A | 4/1995 | Sloan |
| 5,423,334 A | 6/1995 | Jordan |
| 5,423,744 A | 6/1995 | Gencheff et al. |
| 5,425,367 A | 6/1995 | Shapiro et al. |
| 5,425,382 A | 6/1995 | Golden et al. |
| 5,431,161 A | 7/1995 | Ryals et al. |
| 5,446,548 A | 8/1995 | Gerig et al. |
| 5,509,900 A | 4/1996 | Kirkman |
| 5,528,651 A | 6/1996 | Leksell et al. |
| 5,626,630 A | 5/1997 | Markowitz et al. |
| 5,638,819 A | 6/1997 | Manwaring |
| 5,651,043 A | 7/1997 | Tsuyuki et al. |
| 5,680,106 A | 10/1997 | Schrott et al. |
| 5,697,384 A | 12/1997 | Miyawaki et al. |
| 5,707,362 A | 1/1998 | Yoon |
| 5,707,390 A | 1/1998 | Bonutti |
| 5,711,299 A | 1/1998 | Manwaring |
| 5,727,552 A | 3/1998 | Ryan |
| 5,735,795 A | 4/1998 | Young et al. |
| 5,748,767 A | 5/1998 | Raab |
| 5,754,623 A | 5/1998 | Seki |
| 5,757,881 A | 5/1998 | Hughes |
| 5,764,052 A | 6/1998 | Renger |
| 5,769,861 A | 6/1998 | Vilsmeier |
| 5,810,851 A | 9/1998 | Yoon |
| 5,815,076 A | 9/1998 | Herring |
| 5,824,008 A | 10/1998 | Bolduc et al. |
| 5,840,148 A | 11/1998 | Campbell et al. |
| 5,868,673 A | 2/1999 | Vesely |
| 5,879,297 A | 3/1999 | Haynor et al. |
| 5,902,310 A | 5/1999 | Foerster et al. |
| 5,910,144 A | 6/1999 | Hayashi |
| 5,911,717 A | 6/1999 | Jacobsen et al. |
| 5,928,137 A | 7/1999 | Green |
| 5,941,890 A | 8/1999 | Voegele et al. |
| 5,951,481 A | 9/1999 | Evans |
| 5,951,514 A | 9/1999 | Sahota |
| 5,957,934 A | 9/1999 | Rapoport |
| 5,989,265 A | 11/1999 | Bouquet De La Joliniere |
| 6,026,818 A | 2/2000 | Blair et al. |
| 6,059,734 A | 5/2000 | Yoon |
| 6,061,644 A | 5/2000 | Leis |
| 6,066,158 A | 5/2000 | Engelson et al. |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra et al. |
| 6,144,875 A | 11/2000 | Schweikard et al. |
| 6,161,009 A | 12/2000 | Skurdal et al. |
| 6,198,963 B1 | 3/2001 | Haim et al. |
| 6,220,248 B1 | 4/2001 | Voegele et al. |
| 6,222,544 B1 | 4/2001 | Tarr et al. |
| 6,228,055 B1 | 5/2001 | Foerster et al. |
| 6,234,177 B1 | 5/2001 | Barsch |
| 6,246,900 B1 | 6/2001 | Cosman et al. |
| 6,272,371 B1 | 8/2001 | Shlomo |
| 6,307,473 B1 | 10/2001 | Zampini et al. |
| 6,325,758 B1 | 12/2001 | Carol et al. |
| 6,336,904 B1 | 1/2002 | Nikolchev |
| 6,353,655 B1 | 3/2002 | Siochi |
| 6,356,782 B1 | 3/2002 | Sirimanne et al. |
| 6,359,959 B1 | 3/2002 | Butler et al. |
| 6,360,116 B1 | 3/2002 | Jackson, Jr. et al. |
| 6,363,940 B1 | 4/2002 | Krag |
| 6,371,379 B1 | 4/2002 | Dames et al. |
| 6,371,904 B1 | 4/2002 | Sirimanne et al. |
| 6,377,162 B1 | 4/2002 | Delestienne et al. |
| 6,381,485 B1 | 4/2002 | Hunter et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,416,520 B1 | 7/2002 | Kynast et al. |
| 6,425,903 B1 | 7/2002 | Voegele |
| 6,447,448 B1 | 9/2002 | Ishikawa et al. |
| 6,498,944 B1 | 12/2002 | Ben-Haim et al. |
| 6,501,981 B1 | 12/2002 | Schweikard et al. |
| 6,535,756 B1 | 3/2003 | Simon et al. |
| 6,574,492 B1 | 6/2003 | Ben-Haim et al. |
| 6,638,231 B2 | 10/2003 | Govari et al. |
| 6,654,629 B2 | 11/2003 | Montegrande |
| 6,675,810 B2 | 1/2004 | Krag |
| 6,698,433 B2 | 3/2004 | Krag |
| 6,725,083 B1 | 4/2004 | Burbank et al. |
| 6,766,186 B1 | 7/2004 | Hoyns et al. |
| 6,812,842 B2 | 11/2004 | Dimmer |
| 6,822,570 B2 | 11/2004 | Dimmer et al. |
| 6,838,990 B2 | 1/2005 | Dimmer |
| 6,918,919 B2 | 7/2005 | Krag |
| 6,934,356 B1 | 8/2005 | Satheesan et al. |
| 6,937,696 B1 | 8/2005 | Mostafavi |

(56) References Cited

U.S. PATENT DOCUMENTS

| | | |
|---|---|---|
| 6,977,504 B2 | 12/2005 | Wright et al. |
| 6,993,375 B2 | 1/2006 | Burbank et al. |
| 6,999,555 B2 | 2/2006 | Morf |
| 7,026,927 B2 | 4/2006 | Wright et al. |
| 7,027,707 B2 | 4/2006 | Imaki |
| 7,044,957 B2 | 5/2006 | Foerster et al. |
| 7,047,063 B2 | 5/2006 | Burbank et al. |
| 7,135,978 B2 | 11/2006 | Gisselberg et al. |
| 7,142,905 B2 | 11/2006 | Slayton et al. |
| 7,174,201 B2 | 2/2007 | Govari et al. |
| 7,176,798 B2 | 2/2007 | Dimmer et al. |
| 7,206,626 B2 | 4/2007 | Quaid, III |
| 7,206,627 B2 | 4/2007 | Abovitz et al. |
| 7,213,009 B2 | 5/2007 | Pestotnik et al. |
| 7,221,733 B1 | 5/2007 | Takai et al. |
| 7,229,417 B2 | 6/2007 | Foerster et al. |
| 7,280,863 B2 | 10/2007 | Shacher |
| 7,289,839 B2 | 10/2007 | Dimmer et al. |
| 7,318,805 B2 | 1/2008 | Schweikard et al. |
| 7,354,391 B2 * | 4/2008 | Stubbs ................ A61N 5/1015 600/3 |
| 7,397,364 B2 | 7/2008 | Govari |
| 7,447,643 B1 | 11/2008 | Olson et al. |
| 7,534,252 B2 | 5/2009 | Sepetka |
| 7,535,363 B2 | 5/2009 | Gisselberg et al. |
| 7,558,616 B2 | 7/2009 | Govari et al. |
| 7,565,191 B2 | 7/2009 | Burbank et al. |
| 7,590,441 B2 | 9/2009 | Govari |
| 7,599,730 B2 | 10/2009 | Hunter et al. |
| 7,606,405 B2 | 10/2009 | Sawyer et al. |
| 7,625,397 B2 | 12/2009 | Foerster et al. |
| 7,657,301 B2 | 2/2010 | Mate et al. |
| 7,657,302 B2 | 2/2010 | Mate et al. |
| 7,657,303 B2 | 2/2010 | Mate et al. |
| 7,668,582 B2 | 2/2010 | Sirimanne et al. |
| 7,696,876 B2 | 4/2010 | Dimmer |
| 7,729,742 B2 | 6/2010 | Govari |
| 7,778,687 B2 | 8/2010 | Dimmer et al. |
| 7,780,973 B2 | 8/2010 | Freeman et al. |
| 7,912,529 B2 | 3/2011 | Herron et al. |
| 8,046,052 B2 | 10/2011 | Verard et al. |
| 8,060,185 B2 | 11/2011 | Hunter |
| 8,196,589 B2 | 6/2012 | Gisselberg |
| 8,239,002 B2 | 8/2012 | Neustadter et al. |
| 8,239,005 B2 | 8/2012 | Wright et al. |
| 8,277,391 B2 | 10/2012 | Foerster |
| 8,306,602 B2 | 11/2012 | Sirimanne |
| 8,320,993 B2 | 11/2012 | Sirimanne |
| 8,320,994 B2 | 11/2012 | Sirimanne |
| 8,401,616 B2 | 3/2013 | Verard |
| 8,452,375 B2 | 5/2013 | Krag |
| 8,467,853 B2 | 6/2013 | Hunter |
| 8,549,960 B2 | 10/2013 | Hoff |
| 2002/0049394 A1 * | 4/2002 | Roy .................... A61B 5/4504 600/594 |
| 2002/0065461 A1 | 5/2002 | Cosman |
| 2002/0083951 A1 | 7/2002 | Stegmaier |
| 2002/0107437 A1 | 8/2002 | Sirimanne |
| 2002/0165443 A1 | 11/2002 | Mori |
| 2002/0193685 A1 | 12/2002 | Mate et al. |
| 2003/0023161 A1 | 1/2003 | Govari et al. |
| 2003/0117270 A1 * | 6/2003 | Dimmer et al. ............ 340/10.1 |
| 2003/0120150 A1 * | 6/2003 | Govari ................ A61B 5/0031 600/424 |
| 2003/0181794 A1 | 9/2003 | Rini |
| 2003/0192557 A1 | 10/2003 | Krag et al. |
| 2003/0206610 A1 | 11/2003 | Collins |
| 2003/0206614 A1 | 11/2003 | Kendrick et al. |
| 2004/0024304 A1 | 2/2004 | Foerster et al. |
| 2004/0068182 A1 | 4/2004 | Misra |
| 2004/0138555 A1 | 7/2004 | Krag et al. |
| 2005/0004507 A1 | 1/2005 | Schroeppel et al. |
| 2005/0059888 A1 | 3/2005 | Sirimanne et al. |
| 2005/0080338 A1 | 4/2005 | Sirimanne et al. |
| 2005/0080339 A1 | 4/2005 | Sirimanne et al. |
| 2005/0080437 A1 | 4/2005 | Wright |
| 2005/0085895 A1 | 4/2005 | Brown et al. |
| 2005/0101824 A1 | 5/2005 | Stubbs |
| 2005/0113855 A1 | 5/2005 | Kennedy, II et al. |
| 2005/0165305 A1 | 7/2005 | Foerster et al. |
| 2005/0182319 A1 | 8/2005 | Glossop |
| 2005/0273002 A1 | 12/2005 | Goosen et al. |
| 2006/0074443 A1 | 4/2006 | Foerster et al. |
| 2006/0084983 A1 * | 4/2006 | Kim .................... A61B 17/7065 606/914 |
| 2006/0093089 A1 | 5/2006 | Vertatschitsch et al. |
| 2006/0094923 A1 | 5/2006 | Mate et al. |
| 2008/0021308 A1 | 1/2008 | Dimmer et al. |
| 2008/0287781 A1 | 11/2008 | Revie et al. |
| 2009/0259284 A1 | 10/2009 | Yamasaki et al. |
| 2009/0278689 A1 | 11/2009 | Gisselberg et al. |
| 2009/0299174 A1 | 12/2009 | Wright et al. |

FOREIGN PATENT DOCUMENTS

| | | |
|---|---|---|
| WO | WO00/16686 | 3/2000 |
| WO | WO02/39917 | 5/2002 |
| WO | WO04/061460 | 7/2004 |
| WO | WO 2005/067792 A1 | 7/2005 |
| WO | WO05/084572 | 9/2005 |
| WO | WO 2006/020377 A2 | 2/2006 |
| WO | WO07/035798 | 3/2007 |

\* cited by examiner

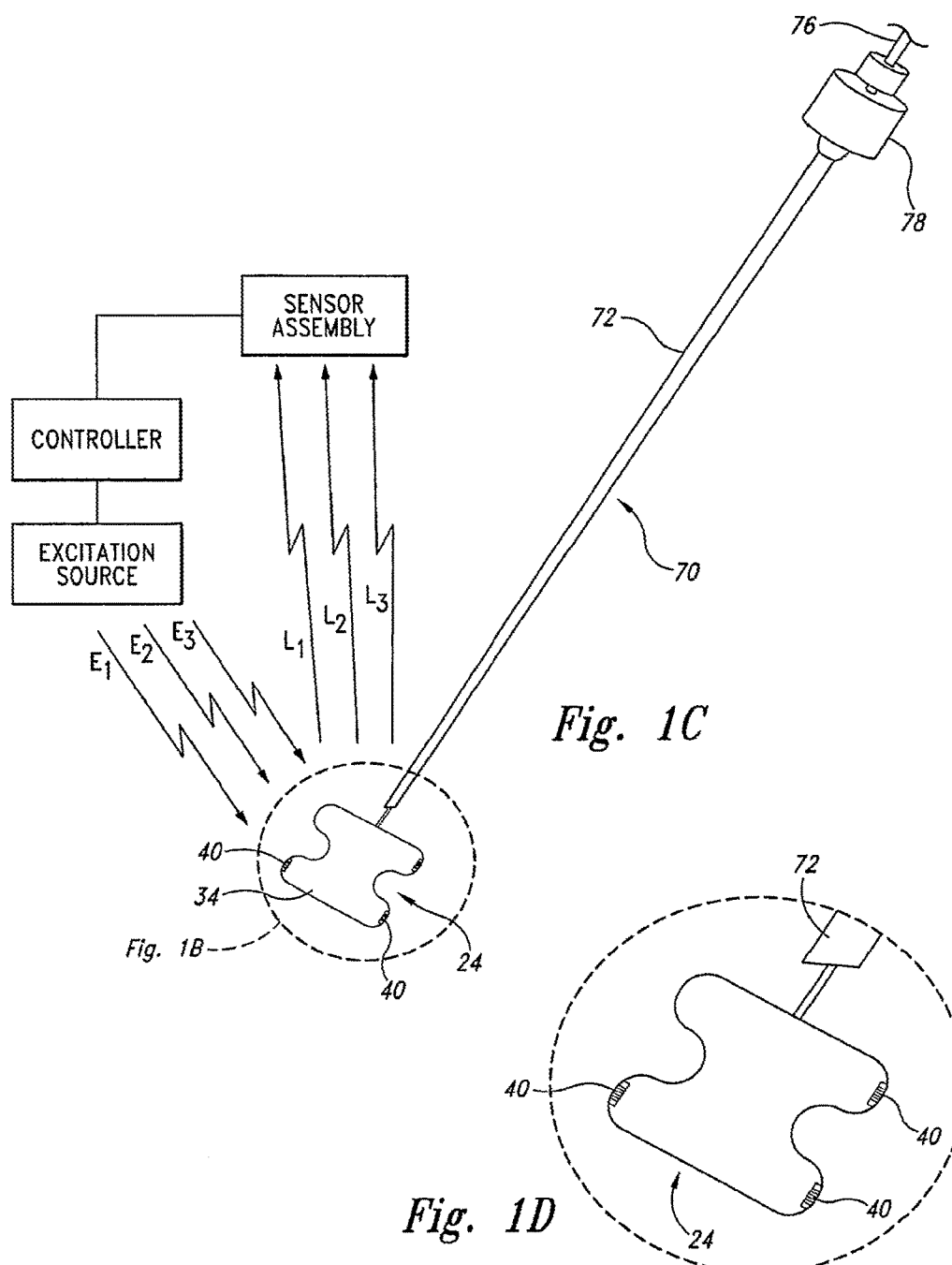

APPARATUS AND METHODS FOR USING AN ELECTROMAGNETIC TRANSPONDER IN ORTHOPEDIC PROCEDURES

CROSS-REFERENCE TO RELATED APPLICATIONS

The present application is a divisional of U.S. patent application Ser. No. 12/159,554, filed Nov. 26, 2008, which was a 371 U.S. National Phase Application of PCT/US2006/044767, with an international filing date of Nov. 17, 2006, which claims the benefit of U.S. Patent Application No. 60/737,907 filed on Nov. 17, 2005. Each of these applications are incorporated herein by reference in their entirety.

TECHNICAL FIELD

Apparatus and methods for using one or more electromagnetic transponders as markers to localize and guide orthopedic procedures including: knee replacement, hip replacement, shoulder replacement, damaged bone reconstruction, and spine surgery, and more particularly, to methods and apparatus for orthopedic surgical navigation and alignment techniques and instruments.

BACKGROUND

One of the main problems in orthopedics today is the lack of accurate position and orientation information during surgery that could be used for registration of implanted devices to bone as well as registering bone structures after diseased or damaged tissue, bone and/or marrow has been removed during a surgical procedure (e.g. knee replacement surgery). For example, the stem of a hip or knee replacement implant should fit within the intramedullary canal of a bone in a manner that approximates the bone structure of the patient. This can be difficult because the bone structure of each patient is slightly different (e.g., different curvature, size, radial orientation, etc.). Although X-rays are typically used to asses the bone structure of a patient, these images do not provide real-time, accurate information during surgery for positioning implants or registering bones in an orientation suited for a specific patient. Therefore, there is a need to provide accurate information to surgeons during a procedure.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIGS. 1A-1I schematically illustrate a spinal stabilization implant having a localization and tracking device in accordance with an embodiment of the invention.

DETAILED DESCRIPTION

A. Overview

Figures 1A, 1B:
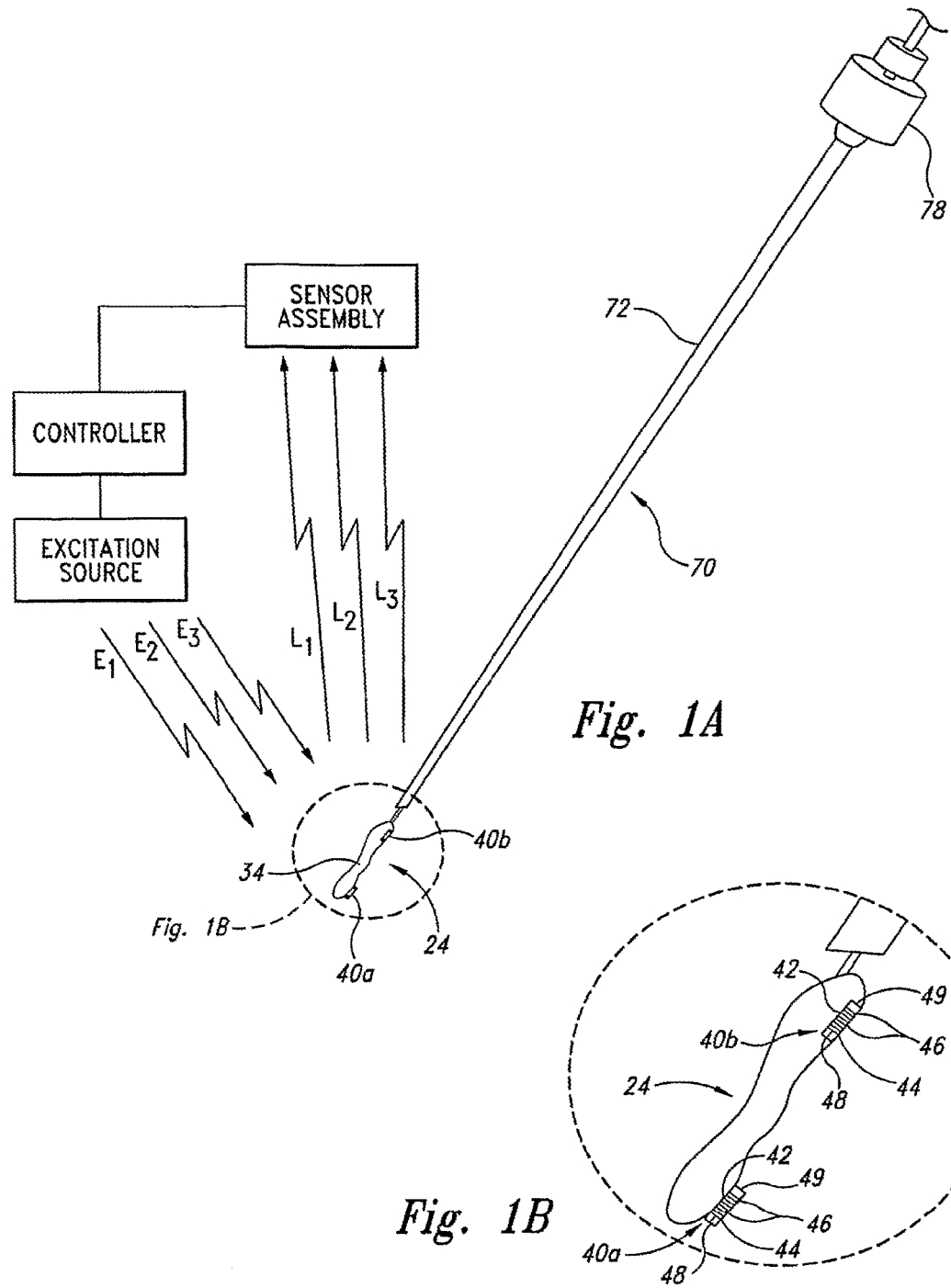

The following disclosure is directed toward surgical guides, prosthesis, implants, and/or instruments including localization markers that (a) are energized by a wirelessly transmitted excitation energy and (b) wirelessly transmit a location signal in response to the excitation energy. Additional aspects of the following description are directed toward methods of using and tracking such instruments implanted or affixed to bony anatomy of a patient, an implant or prosthesis, an intramedullary device, an extramedullary device or a guide, using non-ionizing energy.

One embodiment of a surgical guide, prosthesis, implant and/or instrument in accordance with the invention comprises an elongated member having a distal section configured to be passed through an intramedullary canal of a femur or other passageway in a human. The instrument further includes a magnetic marker having a transponder at the distal section. The transponder includes a circuit configured to be energized by a wirelessly transmitted magnetic excitation energy and to wirelessly transmit a magnetic location signal in response to the excitation energy. The magnetic transponder of the marker includes a circuit configured to (a) be energized by a wirelessly transmitted pulsed magnetic field and (b) wirelessly transmit a pulsed magnetic location signal in response to the pulsed magnetic field. The magnetic marker, for example, can be attached to or otherwise integral with the elongated member.

Another aspect of the following disclosure is directed toward systems for tracking an implant in a patient or guide associated with the bony anatomy of the patient. One embodiment of such a system includes an elongate member having an elongated rod with a distal section configured to be passed through an intramedullary canal in a human and a magnetic marker having a transponder at the distal section of the member. Another embodiment of such a system includes an orthopedic implant having a magnetic marker in, affixed to or in a substantially fixed relationship to the implant. Another embodiment of such a system includes a guide for use during orthopedic surgery, the marker in a substantially fixed relationship to the guide. The transponder has a circuit configured to (a) be energized by a wirelessly transmitted pulsed magnetic field and (b) wirelessly transmit a pulsed magnetic location signal in response to the pulsed magnetic field. The system further includes an excitation source comprising an energy storage device, a source coil, and a switching network coupled to the energy storage device and the source coil. The source coil is configured to wirelessly transmit the pulsed magnetic field to energize a transponder. The switching network is configured to alternately transfer (a) stored energy from the energy storage device to the source coil and (b) energy in the source coil back to the energy storage device.

Another aspect for tracking an implant in a patient or guide associated with the bony anatomy of the patient includes an implant or guide as set forth above and a sensor assembly comprising a support member and a plurality of field sensors carried by the support member. The field sensors are at least substantially locally planar relative to one another to sense the pulsed magnetic location signal from the transponder. The field sensors can be responsive only to field components of the pulsed magnetic location signal normal to individual field sensors. In other embodiments, the field sensors are arranged in an array occupying an area having a maximum dimension of approximately 100% to 300% of a predetermined sensing distance between the marker and the sensing array.

Additional aspects of the invention are directed toward methods for guiding the prosthesis, implant, guide or other instrument. One embodiment of such a method comprises implanting the prosthetic in a patient and tracking the implant as it is implanted. According to further aspects, the implant can include one or a plurality of markers. Alternatively, the implant may be implanted in a collapsed or unexpanded state and may be expanded after positioning the implant in the patient. According to aspects of this embodiment, the implant may be initially tracked for purposes of placement and may be further tracked to confirm appropriate expansion of the implant. The implant is tracked as is placed in the patient by (a) wirelessly delivering a pulsed magnetic field to energize the marker, (b) wirelessly transmitting a pulsed location signal from the marker, (c) sensing the pulsed location signal at a sensor located outside the patient, and (d) periodically calculating a three-dimensional location of the marker in a reference frame. The method can further include providing an output of the location of the marker in the reference frame at least every tf second and within tl second from sensing the pulsed location signal. In many embodiments, tf and tl are not greater than one second.

According to other aspects of the invention, the radiographic center of a marker coincide with the magnetic center of a transponder of the marker. If the radiographic center coincides with the magnetic center of the transponder, the transponders can be localized on X-ray or CT prior to surgery. After X-ray or CT, the surgery can be planned using the preoperative X-rays. Next, the markers may be localized intraoperatively with electromagnetic tracking. Finally, the markers can be localized during physical therapy to monitor recovery as well as longer term follow-up activities.

According to further aspects of the invention, a plurality of electromagnetic markers are used to provide three dimensional position information (X, Y and Z position) as location fiducials for implants, guides, prosthesis and the like. As additional markers are used, the dimensionality of localization, alignment and registration solutions increases. For example, a single marker defines a single position in localization space; two markers can be used to register the distance between two points. Furthermore, two independent sets of two rigidly mounted markers can be used to register and align two vectors relative to each other. And, three markers rigidly mounted relative to each other can be used to define a plane including rotational angles of the plane (i.e. pitch, yaw and roll). Suitable markers include, for example, the markers shown and described in U.S. Pat. Nos. 6,918, 919 and 6,822,570; and U.S. application Ser. Nos. 10/334, 700; 09/954,700; 10/679,801; 10/382,123; 10/745,097; 10/746,888; and 11/166,801, all of which are incorporated herein by reference.

B. Tracking Systems and Methods for Spinal Stabilization Devices

FIG. 1A illustrates a spinal stabilization device in an unexpanded or collapsed state coupled to a cannula of the delivery system. FIG. 1B is an enlarged view of the spinal stabilization device of FIG. 1A. FIGS. 1C and 1D illustrates the spinal stabilization device in an expanded state coupled to a cannula of the delivery system. FIG. 1D is an enlarged view of the spinal stabilization device of FIG. 1A. The spinal stabilization device further includes a magnetic marker 40 having a transponder with a circuit configured to be energized by a wirelessly transmitted magnetic excitation energy and to wirelessly transmit a magnetic location signal in response to the excitation energy. The marker 40 enables the spinal stabilization device to be tracked in the patient using a non-ionizing energy and without electrically coupling the marker to a sensor or excitation source. The spinal stabilization device, therefore, is expected to significantly improve the ability to implant or otherwise guide devices through patients in many medical procedures. As explained in more detail below, the marker 40 can be attached to the implant and/or imbedded in the implant depending upon the particular application. According to further aspects of the invention, a plurality of magnetic markers can be attached to the implant and/or imbedded in the implant.

A system of the present invention includes a cannula device 70 having an outer sheath 72, a proximal hub 78 and preferably at least two interior lumens 74, 76 for the percutaneous delivery the device and other tools as are know in the art for implanting the spinal device.

As shown in FIGS. 1A-1C, an exemplary spinal stabilization device 24 is illustrated in collapsed and expanded configurations, respectively. According to aspects of the invention, the spinal stabilization device can be tracked during implantation in the collapsed state to confirm the location of the device prior to expanding the device. Exemplary spinal stabilization device 24 includes an expandable spacer body 24 that has a size and shape when in the expanded condition for operative positioning between the spinous processes of adjacent superior and inferior vertebrae of the spinal motion segment being treated.

The marker 40 illustrated in FIGS. 1A and 1B is a magnetic marker including a transponder 42 having a core 44, a coil 46 around the core 44, and a capacitor 48 electrically coupled to the coil 46. The core 44 is typically composed of ferrite, and the coil 46 includes a plurality of windings of a wire around the core 44. The transponder 42 can be contained in a capsule 49. The transponder 42 generally has a small cross-sectional dimension so that the collapsed spinal device 24 can pass through small entry ports. For example, the transponder 42 can have a cylindrical portion with a diameter from approximately 0.5-3 mm, and desirably from 0.5-2 mm. The transponder 42 is a resonating circuit that receives the wirelessly transmitted magnetic excitation energy and produces a wirelessly transmitted location signal in response to the excitation signal. The transponder 42 accordingly has a resonant frequency at which the magnetic excitation energy energizes the transponder 42. Several embodiments of instruments with the marker 40, as well as specific embodiments of markers 40, are described below with reference to FIGS. 2A-9.

Spinal spacers can be made of an inflatable non-porous material, i.e., balloon type spacers are inflated with an inflation or expansion medium, such as air, saline, another biologically compatible fluid, or a flowable solid material, such as polyurethane, or a gel, which thickens or hardens substantially upon injection into balloon 34. The marker 40 is contained in a capsule 49 and therefore can be contained within the balloon type spacer or affixed to the surface of the balloon type spacer as described further below in reference to FIGS. 1E and 1F. In one embodiment, balloon 34 is initially inflated with air to provide some structure or rigidity to it to facilitate its optimum positioning and alignment between the spinous processes. Once positioned as desired, balloon 34 is injected with a flowable solid material (the air therein being displaced possibly via a vent hole within port 32). In certain embodiments, the expandable body is made of a non-compliant or semi-compliant material so as to maintain a substantially fixed shape or configuration and ensure proper, long-term retention within the implant site. In other embodiments, the expandable member may be made of a compliant material. In any embodiment, the compressibility and flexibility of balloon 34 can be selected to address the indications being treated. When unexpanded or deflated, expandable body 34 has a low profile, such as a narrow, elongated shape, to be easily translated through a delivery cannula 70. The shape of expandable body 34, when in an expanded or inflated state, has larger profile which is generally H-shaped.

According to aspects of the invention, the markers may be incorporated into other spinal stabilization devices, for example, the expandable spine stabilization system in U.S. Publication No. 2005/0171543 entitled Spine Stabilization Systems and Associated Devices, Assemblies and Methods; U.S. Publication No. 2006/0084988 entitled System and Methods for Posterior Dynamic Stabilization of the Spine; U.S. Publication No. 2006/0241614 entitled Implants and Methods for Posterior Dynamic Stabilization of a Spinal Motion Segment; U.S. Publication No. 2006/0241613 entitled Implants and Methods for Inter-Transverse Process Dynamic Stabilization of a Spinal Motion Segment; U.S. Publication No. 2006/0229608 entitled Apparatus and Methods for Spinal Implant with Dynamic Stabilization System; U.S. Publication No. 2006/0085069 entitled Systems and Methods for Posterior Dynamic Stabilization of the Spine; U.S. Publication No. 2006/0084987 entitled Systems and Methods for Posterior Dynamic Stabilization of the Spine; U.S. Publication No. 2006/0111715 entitled Dynamic Stabilization Assemblies, Tool Set and Method; U.S. Publication No. 2006/0084985 entitled Systems and Methods for Posterior Dynamic Stabilization of the Spine; U.S. Publication No. 2006/0084984 entitled Systems and Methods for Posterior Dynamic Stabilization of the Spine; U.S. Publication No. 2006/0084983 entitled Systems and Methods for Posterior Dynamic Stabilization of the Spine; U.S. Publication No. 2006/0084982 entitled Systems and Methods for Posterior Dynamic Stabilization of the Spine; U.S. Publication No. 2006/0079898 entitled Spinal Motion Preservation Assemblies; U.S. Publication No. 2006/0058800 entitled Methods and Apparatus for Provision of Therapy to Adjacent Motion Segments; U.S. Publication No. 2006/0036240 entitled System and Method for Dynamic Skeletal Stabilization.

Figure 1E:
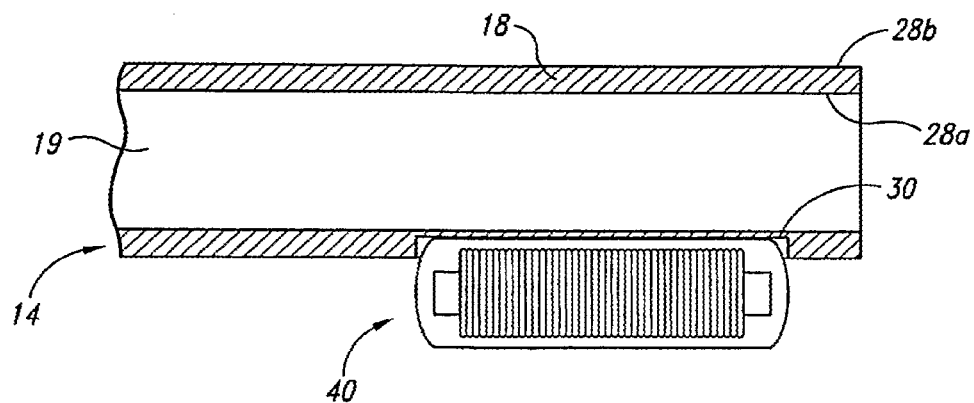
Figure 1F:
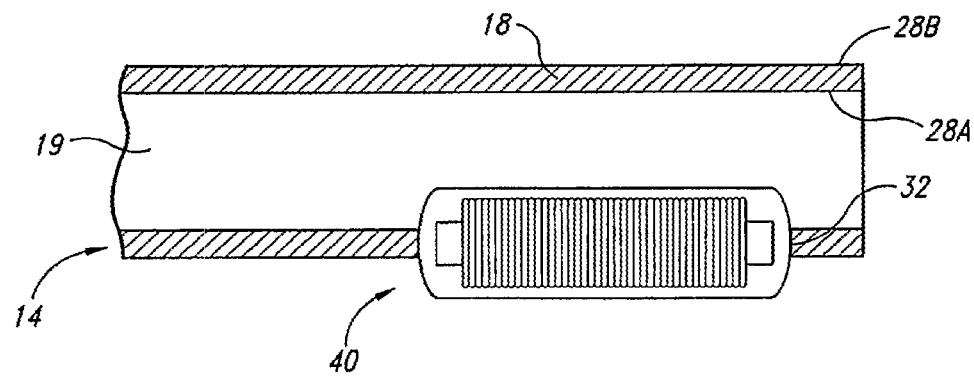

FIGS. 1E and 1F are cross-sectional views illustrating additional embodiments of the spinal device 24 (FIG. 1A) in which the marker 40 is attached to the spinal device 24. In the embodiment shown in FIG. 1E, a distal section 18 of the spinal device has an inner surface 28a defining a lumen 19, an outer surface 28b, and a recess 30 in the outer surface 28b. The recess 30 extends to an intermediate depth in the wall between the inner surface 28a and the outer surface 28b. At least a portion of the marker 40 is attached to the spinal device 24 using an adhesive, weld or fastener to adhere the marker 40 to the recess 30 in the spinal device 24. Referring to FIG. 1F, this embodiment is similar to the embodiment shown in FIG. 1E, but the spinal device 24 includes a hole 32 through the wall between the inner surface 28a and the outer surface 28b. In this embodiment, the marker 40 is attached to the hole 32 using an adhesive or other material. One aspect of the embodiments illustrated in FIGS. 1E and 1F is that at least a portion of the marker 40 resides within the wall of the spinal device 24. This reduces the cross-sectional area of the lumen 19 occupied by the marker 40 and/or reduces the overall cross-sectional dimension of the distal section 18 of the spinal device 24 where the marker 40 is located.

Figure 1G:
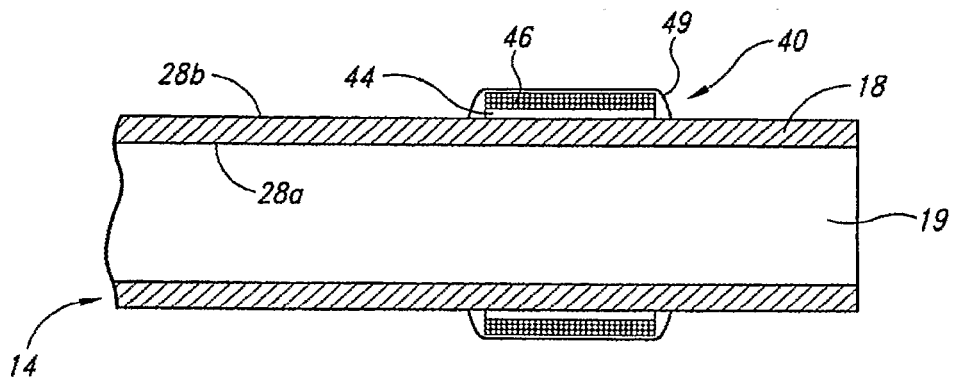
Figure 1H:
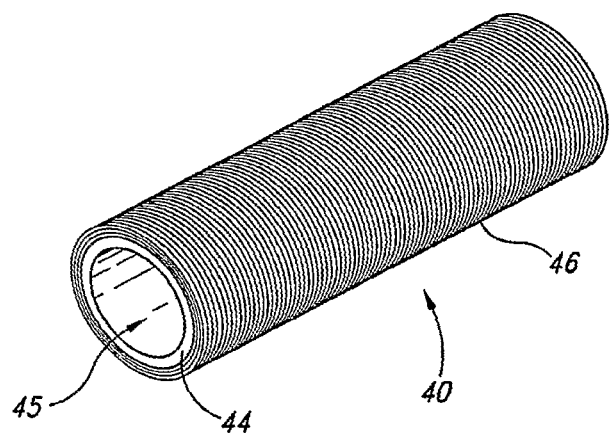

FIG. 1G is a cross-sectional view illustrating a distal section of an instrument in accordance with another embodiment of the invention, and FIG. 1H is an isometric view of an embodiment of a marker for use with the instrument illustrated in FIG. 1G. In this particular embodiment, the marker 40 includes a tubular core 44 having a bore 45 (FIG. 1H) configured to receive the outer surface 28b of the spinal device 24 (FIG. 1G). The coil 46 is wrapped around the tubular core 44, and the capsule 49 or other coating encases the tubular core 44 and the coil 46. The marker 40 illustrated in FIGS. 1G and 1H can further include a capacitor as described above with reference to the marker 40 illustrated in FIG. 1.

Figure 1I:
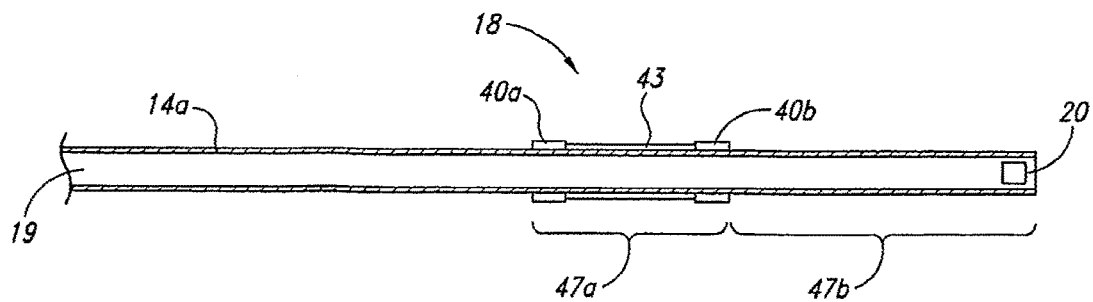

FIG. 1I is a cross-sectional view illustrating an instrument in accordance with another embodiment of the invention. The instrument in this embodiment can be used in any of the minimally invasive surgical techniques used in spine, joint, or other orthopedic surgeries. In this embodiment, the instrument has a body 14a having a distal section 18 that is configured to be inserted into a patient. The body 14a can be a rigid or flexible member depending on whether the instrument is a probe, catheter, electrode, ablation tool, welding tool, sensor, or other diagnostic or therapeutic tool. In the case of a catheter, a significant portion of the body 14a is flexible and has a lumen 19. The instrument may further include a therapeutic or diagnostic device 20 at the distal section 18.

The instrument illustrated in FIG. 1I has two markers 40a and 40b positioned apart from one another along the body 14a. The markers 40a-b can be any of the markers illustrated above with respect to the Figures. For example, the marker 40 illustrated in FIGS. 1G and 1H can be positioned on the outer wall of the body 14a (shown in FIG. 1E) or the inner wall of the lumen 19 (not shown). The markers 40a-b are aligned along a longitudinal axis of the body 14a. The markers 40a-b, more specifically, are typically aligned with the central axis of the body 14a, but in other embodiments the markers 40a-b can be aligned with each other along an off-center axis. In still other embodiments, the markers 40a-b can be axially offset from each other along different axes of the body 14a. When the body 14a is flexible, the instrument can further include a rigid support 43 in the region of the markers 40a-b. The rigid support 43 can be a sleeve on the inner wall or outer wall of the body 14a. The rigid support 43 can alternatively be a thickened portion of the body 14a. The distal section 18 of the instrument accordingly has a first portion 47a and a second portion 47b. The first portion 47a is rigid to maintain the relative orientation between the markers 40a-b, but the second portion 47b can be rigid or flexible depending upon the particular application. For example, the second portion 47b of the distal section 18 may be a flexible tip to make it easier to pass the instrument through small or torturous passageways in a patient.

The instrument shown in FIG. 1I provides a directional vector indicative of the location and angular orientation of the distal section 18 as the instrument is guided through the patient. The rigid support 43 maintains the distance and axially alignment between the markers 40a-b. As a result, by knowing the three-dimensional coordinates of each marker 40a-b in a reference frame and the relative positions between the markers 40a-b, a vector can be established that defines the position and orientation of the distal section 18 of the instrument with two degrees of orientation. The projection of the vector defined by the markers 40a-b can be used to localize the tip of the distal section 18 that houses the therapeutic or diagnostic device 20. As a result, the instrument illustrated in FIG. 1I is expected to enhance the ease and accuracy with which a therapeutic or diagnostic device is positioned within a patient.

C. Tracking Systems and Methods Used for Other Implant Devices or in Bony Anatomy According to further aspects of the invention, electromagnetic markers could be used in orthopedic surgical applications such as a marker affixed to in-situ bone or to an implant; in a fixed relationship with a surgical guide to provide objective, real-time location information to allow more accurate surgical cuts of existing bone, length, rotation; during surgery to assure alignment and/or post surgery to confirm implant positioning and range of motion; in a bone screw to guide positioning of the screw, guide removal of the screw, or monitor implanted position of the screw.

The marker could further be used in any number of guides or templates that attach to the bony anatomy, such as a surgical guide, cutting guide, cutting jig, resection block and/or resurfacing guide. For example, the marker could be incorporated into an existing intramedullary guide rod for a femur and an extramedullary guide rod for a tibia in a knee replacement surgery; or into an external surgical guide system, or the marker could eliminate the need for an external template altogether. According to yet another anticipated use of the tracking system, the marker could be used in conjunction with or replace an optical alignment system. Templates or guides are commonly used in orthopedic surgery of the spine, joints (e.g. knee or hip), and trauma.

Figure 2:
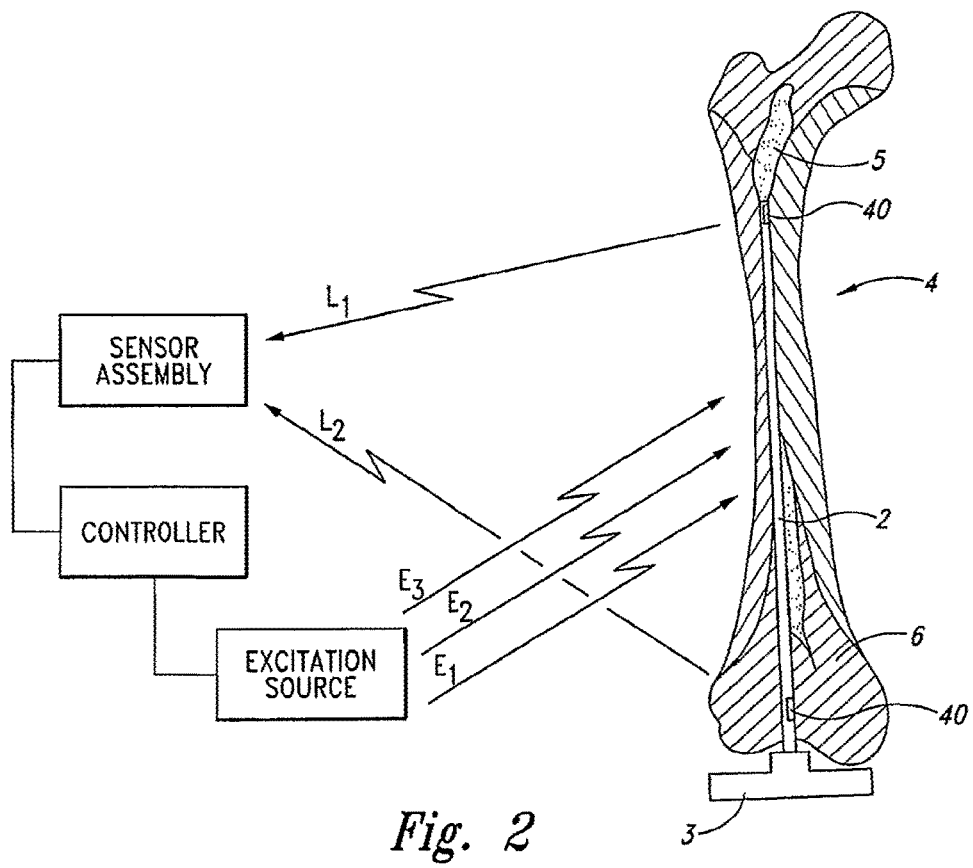
FIG. 2 schematically illustrates a intramedullary alignment guide having a localization and tracking device in accordance with an embodiment of the invention.

FIG. 2 shows, in cross-section, an intramedullary alignment guide 2 having a handle, a femur 4 having a tubular shaft of cortical bone surrounding intramedullary canal 5 and having areas of spongy bone 6 at both ends of the shaft. The intramedullary alignment guide can further include markers 40 such as the electromagnetic markers disclosed herein, in combination with a sensor assembly, controller and excitation source, in order to track the position of the intramedullary device. The markers 40 may be integrally formed with the intramedullary alignment guide, may be contained on a cap or extension (not shown) of the intramedullary alignment guide, or may be otherwise contained in a substantially fixed relationship to the alignment guide. One example of a suitable intramedullary alignment guide is found in U.S. Pat. No. 4,474,177 entitled Method and Apparatus for Shaping a Distal Femoral Surface. Other suitable alignment guides are found in U.S. Pat. Nos. 4,718,413; 4,892,093; 5,454,816; 5,474,559; 5,601,563; 5,653,714, 6,712,824; 6,558,391; and U.S. Patent Publication Nos. 2002/0133163, 2005/0021039 and 2003/0100907 each of which are incorporated herein.

According to aspects of the invention, a tracking system for use in orthopedic surgeries and other procedures provides objective internal alignment data (inflection, flexure, rotation, overall mechanical alignment) from bone (registration problem) for clinical confidence (need to take acquisition reference points away from cut). According to further aspects of the invention, relative position of remaining bone components can be confirmed once an initial cut has been made so that the completed replacement joint maintains correct position and rotation of bone components relative to each other (e.g. tibia and femur bone components in knee replacement surgery). Poor initial placement is the primary reason for replacement joints to fail in patients.

According to further aspects of the invention, an easier way to integrate image data into a computer guided cutting and implantation surgical process is provided. For example, as detailed further below with, the system can provide data for use in treatment planning to increase the accuracy of the surgery, for a patient communication tool, and to reduce the duration of the surgery. In addition, orthopedic surgery is generally trending toward minimally invasive surgery (MIS), a surgical technique that allows the surgeon to see less of the surgery site. The tracking system of the present invention will provide significant benefits in a surgery technique that increases the risk of misalignment due to reduced visibility. By providing objective tracking and alignment data, minimally invasive knee replacement surgery and other minimally invasive surgeries will be practical for mainstream surgeons.

One expected advantage of a tracking system for implants, guides and other orthopedic devices used in surgeries is the ability to rely on objective internal alignment data for bone increasing confidence for first cut. Additional advantages of obtaining objective internal alignment data includes confirmation of the relative position once an initial cut has been made. A further advantage is the ability to integrate image data into computer guided surgery. Yet another advantage is the enablement of treatment planning with preoperative x-ray or CT. Still another advantage is the enablement of accurate and precise image guided surgery for alignment of bone components during surgery.

According to further aspects of the invention, the markers can be implanted in or relative to bone components of interest and used after surgery to monitor healing and/or physical therapy progress without any detrimental effects to the patient such as x-ray radiation According to aspects of the invention, the electromagnetic tracking system may be combined with an optical system to provide increased accuracy and ease of use. The combination system is advantageous over standard optical tracking for at least the following reasons: there are no line of sight issues; the electromagnetic markers can resonate at different frequencies and are distinguishable from each other by the system, the electromagnetic markers are a better proxy for the location of the implant than just the implant.

Figure 3:
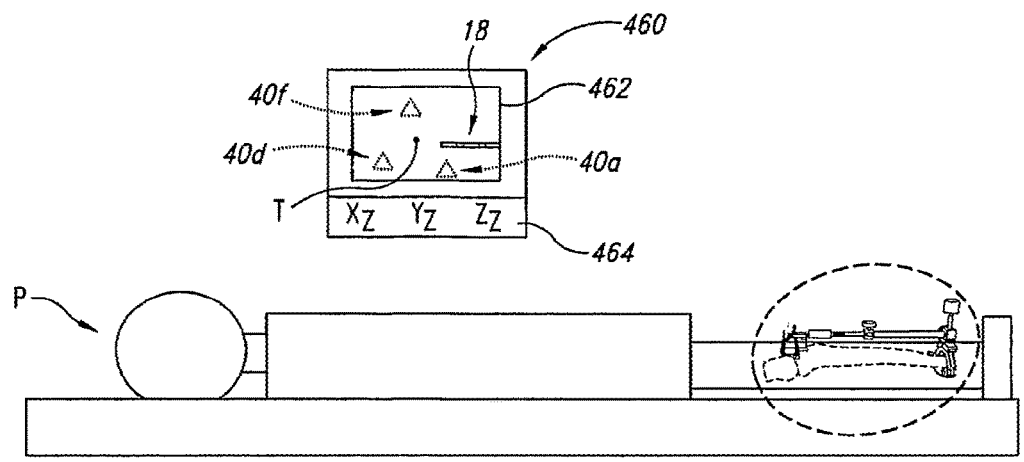
FIG. 3 schematically illustrates an alignment guide having a localization and tracking device in accordance with an embodiment of the invention.

As shown in FIG. 3, markers 40 are used in combination with guide systems to provide tracking. The markers 40 may be implanted in the bone or may be contained in a fixed relationship with the guide system or may be integrated with the guide system or may be a combination of one or more of these.

Exemplary work flow for a knee replacement surgery:
Pre-Surgery
1. X-Ray (diagnostic+markers) (image overlay)
1a. Treatment planning tool
Surgery
2. Pre-registration. Localization framework (template or temporary guidance rod)
3. Data acquisition
4. Tibia/Femur planning pre-cut
5. Cut
5a. Remove intramedullary guide rod
6. Implant Placement
7. Ligament balancing

D. Systems and Procedures of a Localization and Tracking System

Figure 4A:
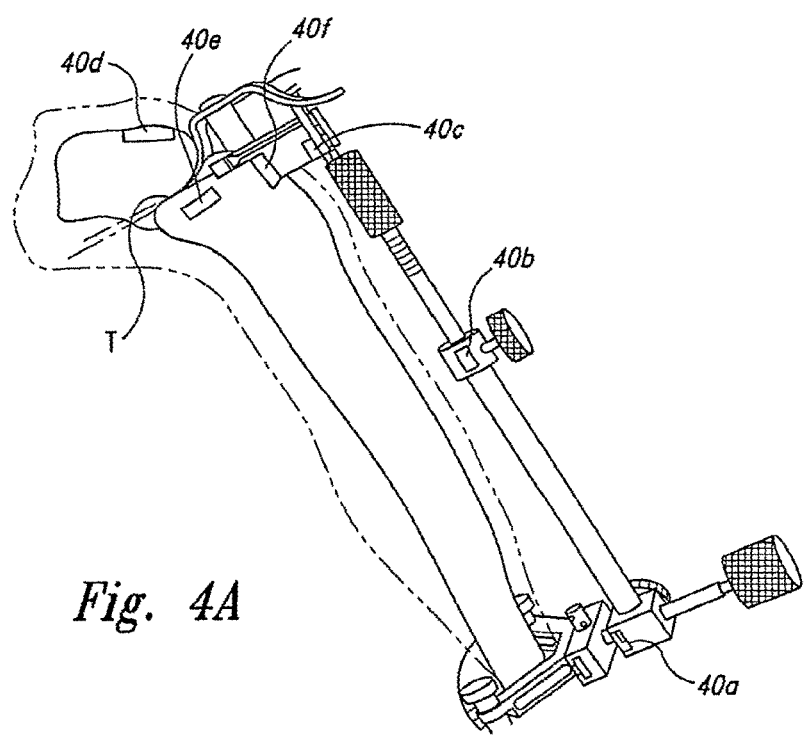
FIG. 4A schematically illustrate implant, guide and/or minimally invasive surgical instruments and a localization system in accordance with various embodiments of the invention.

FIG. 4A is a schematic view illustrating an embodiment of a localization system for use with any of the embodiments of the instrument 10 illustrated and/or described above with reference to FIGS. 1-3. In this particular embodiment, the instrument 10 includes a plurality of markers 40 (identified individually as a first marker 40a, a second marker 40b and a third marker 40c). The markers 40a-c are used to determine the location and configuration of the implant, guide or minimally invasive surgical instrument 10 as it is being inserted into the patient and/or after the implant, guide or instrument 10 has been located at the target site.

The localization system includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 40a-c on the instrument 10. The embodiment of the excitation source 60 shown in FIG. 4A produces a pulsed magnetic field at different frequencies. For example, the excitation source 60 can frequency multiplex the magnetic field at a first frequency E1 to energize the first marker 40a, a second frequency E2 to energize the second marker 40b, and a third frequency E3 to energize the third marker 40c. In response to the excitation energy, the markers 40a-c generate location signals L1-3, respectively, at unique response frequencies. More specifically, the first marker 40a generates a first location signal L1 at a first frequency in response to the excitation energy at the first frequency E1, the second marker 40b generates a second location signal L2 at a second frequency in response to the excitation energy at the second frequency E2, and the third marker 40c generates a third location signal L3 at a third frequency in response to the excitation energy at the third frequency E3.

The sensor assembly 70 can include a plurality of coils to sense the location signals L1-3 from the markers 40a-c. The sensor assembly 70 can be a flat panel having a plurality of coils that are at least substantially coplanar relative to each other. In other embodiments, the sensor assembly 70 may be a nonplanar array of coils.

The controller 80 includes hardware, software or other computer-operable media containing instructions that operate the excitation source 60 to multiplex the excitation energy at the different frequencies E1-3. For example, the controller 80 causes the excitation source 60 to generate the excitation energy at the first frequency E1 for a first excitation period, and then the controller 80 causes the excitation source 60 to terminate the excitation energy at the first frequency E1 for a first sensing phase during which the sensor assembly 70 senses the first location signal L1 from the first marker 40a without the presence of the excitation energy at the first frequency E1. The controller 80 also causes the excitation source 60 to (a) generate the second excitation energy at the second frequency E2 for a second excitation period and (b) terminate the excitation energy at the second frequency E2 for a second sensing phase during which the sensor assembly 70 senses the second location signal L2 from the second marker 40b without the presence of the second excitation energy at the second frequency E2. The controller 80 replicates this operation with the third excitation energy at the third frequency E3 such that the third marker 40c transmits the third location signal L3 to the sensor assembly 70 during a third sensing phase. As such, the excitation source 60 wirelessly transmits the excitation energy in the form of pulsed magnetic fields at the resonant frequencies of the markers 40a-c during excitation periods, and the markers 40a-c wirelessly transmit the location signals L1-3 to the sensor assembly 70 during sensing phases.

The computer-operable media in the controller 80, or in a separate signal processor, also includes instructions to determine the absolute positions of each of the markers 40a-c in a three-dimensional reference frame. Based on signals provided by the sensor assembly 70 that correspond to the magnitude of each of the location signals L1-3, the controller 80 and/or a separate signal processor calculate the absolute coordinates of each of the markers 40a-c in the three-dimensional reference frame.

One procedure for tracking the prosthesis, guide and/or instrument 10 through the patient includes attaching reference markers 40d-f to the patient and acquiring reference images showing the position of the reference markers 40d-f relative to the target site using MRI images, CT images, radiographic images or other suitable types of images. The reference markers 40d-f can be adhered to the patient using an external patch, implanted in tissue, or otherwise anchored to the bone structure of the patient. The instrument 10 is then implanted in the patient by moving the distal section 18 of the spinal device 24 through a desired vessel or other passageway. As the instrument 10 is inserted into the patient, the markers 40a-f are individually energized by the excitation source 60 at six different frequencies, and the sensor assembly 70 receives independent location signals from each of the markers 40a-f. The controller 80 and/or a separate signal processor then calculates the absolute position of each marker in a three-dimensional reference frame. The controller 80 can also calculate (a) the location of the device 20 using the absolute locations of the markers 40a-c and (b) the location of the target site using the absolute locations of the reference markers 40d-f. Based on the calculated locations of the markers 40a-c and the target site, the controller 80 can further calculate the relative offset between these items in real time.

The instrument 10 and localization system enable a practitioner to track the location of the instrument 10 relative to the target site as it is being implanted into the patient and at any time after implantation. The location system illustrated in FIG. 4A can calculate the absolute position of each individual marker 40 at a frequency of approximately 1 ms to 1.0 second. Additionally, the location system can provide the absolute locations of the markers 40, the device 20 carried by the instrument 10, and/or the target site either individually or relative to one another within a latency of 10 ms to 2 seconds from the time the localization signals were transmitted from the markers 40. The location system accordingly provides real-time tracking to an operator to ensure that the instrument 10 and/or the device 20 pass through the desired passageway and are positioned accurately within the patient without ionizing radiation.

Figure 4B:
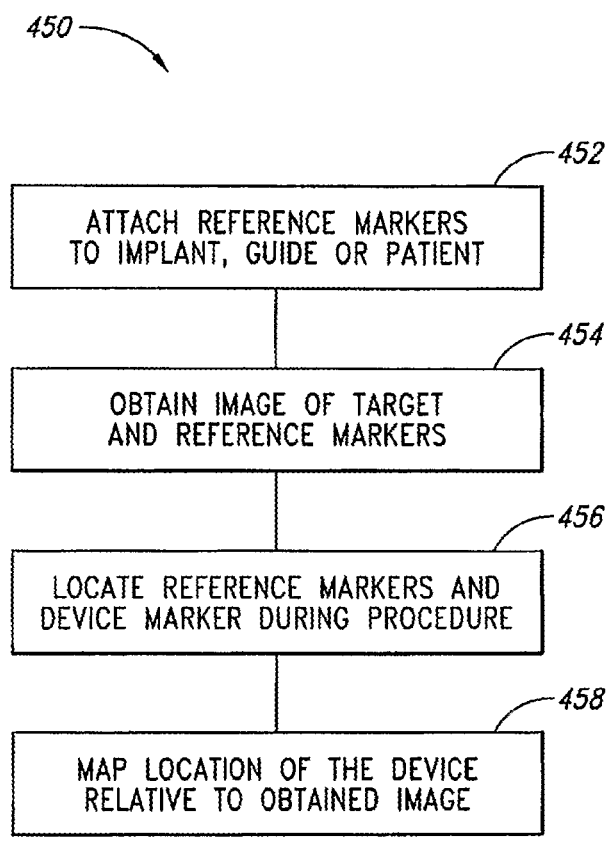
FIG. 4B is a flow chart illustrating another method of using instruments and localization systems in accordance with the invention.

FIG. 4B is a flow chart illustrating a method 450 of using an instrument in accordance with an embodiment of the invention, and FIG. 3 is a schematic view illustrating aspects of an embodiment of the method 450. The method 450 for performing a diagnostic or therapeutic procedure on a patient includes a first stage 452 in which reference markers 40d-f (FIG. 3) are attached to a patient P. The method 450 further includes a second stage 454 that includes obtaining one or more reference images showing the position of the reference markers 40d-f relative to the target T using MRI images, CT images, radiographic images, ultrasonic images, or other suitable types of images as explained above with reference to FIG. 4A. The reference markers 40d-f can be adhered to the patient using an external patch, implanted in tissue, or otherwise anchored to the bone structure of the patient. One aspect of the first and second stages 452 and 454 is that the markers 40d-f can be attached to the patient during a diagnostic stage of treating the patient before obtaining the reference images. The markers can then be left in the patient for a long period of time because they are not hard-wired to any external excitation or sensing devices. The patient can accordingly be moved for further diagnostic procedures or therapeutic procedures at a later time or in a different location.

The method 450 continues with a third stage 456 in which the reference markers 40d-f and device markers 40a-b (FIG. 3) are located during a diagnostic and/or therapeutic procedure. The reference markers 40d-f and device markers 40a-b shown in FIG. 3 can be located simultaneously, or at least substantially simultaneously, in real time during the procedure as described above with reference to FIG. 4A. The method 450 further includes a fourth stage 458 in which the location of the cutting device 20 is mapped or otherwise presented relative to the target T by superimposing a representation of the instrument on a display of a reference image that was previously obtained.

The fourth stage 458 of the method 450 can have several different embodiments. Referring to FIG. 3, for example, the system can further include a display 460 that provides an image 462 that has been registered to the proper orientation using the reference images that were obtained in the earlier stages of the method and a reference frame defined by the reference markers 40d-f (shown in phantom in the image 462). The position of the distal section 18 of the cutting device 20 can be mapped (e.g., superimposed) onto the registered image 462 to illustrate the relative orientation between the instrument and the target T. The display 460 can further include alphanumeric indicators 464 illustrating the relative displacement between the distal section 18 of the instrument and the target T. U.S. Pat. Nos. 5,729,129 and 6,161,032, which are herein incorporated by reference, disclose processes for displaying the position of the cutting device 20 on the display 460 by superimposing a representation of the device on previously acquired images of the patient.

The systems and methods set forth above with respect to FIGS. 4A and 4B that use wireless markers provide several advantages over conventional systems using wired transponders. For example, U.S. Pat. Nos. 5,729,129 and 6,161,032 disclose "wired" systems in which magnetic field sensors attached to the patient or a probe are hard-wired to a receiver to detect the position and orientation of medical probes within the body of a patient. U.S. Pat. No. 6,161,032 discloses a system having a wired field transmitter attached to the end of a probe (e.g., a catheter), three wired reference assemblies that can be attached to the patient, and a calibration array that is separate from the patient. In a typical application, it appears that a patient initially undergoes a diagnostic procedure in which the target (e.g., a soft tissue lesion) is imaged. The patient then proceeds to a therapeutic procedure at a later point in time during which the wired reference assemblies are attached to desired locations on the patient. The system is then calibrated with the patient in position for the therapy by locating the wired reference assemblies using either a calibration array or a probe that is manually placed on the reference assemblies. The image of the patient is then registered with respect to the external reference frame defined by the three reference assemblies. At this point, the patient is then ready to actually undergo the therapeutic procedure in which the probe is located relative to the reference transducers. The position of the probe is then mapped to the image to provide the practitioner a visual representation of the relative position between the probe and the target.

One problem with such wired systems is that the reference assemblies are attached to the patient after obtaining the diagnostic images. The system is thus manually calibrated before performing the therapeutic procedure. This is a relatively time consuming aspect of the procedure that reduces the utilization of expensive equipment and facilities associated with surgical or therapeutic procedures. Another problem with such systems is that the reference assemblies may not be accurately positioned relative to the target such that the external reference frame defined by the reference assemblies introduces systemic errors that decrease the accuracy of the measurements. Therefore, wired magnetic tracking systems are not expected to provide satisfactory results for many applications.

In contrast to the wired systems, the systems and methods set forth in FIGS. 4A and 4B that use wireless markers increase the utilization of expensive facilities and accurately localize the instrument. The reference markers 40d-f of the system illustrated in FIG. 3 are accurately imaged and localized during an initial diagnostic stage of a therapy. This eliminates having to calibrate the system and determine the reference frame while a patient is positioned at a treatment site immediately before a treatment as required in U.S. Pat. No. 6,161,032. As a result, the inventive systems and methods increase the utilization of expensive operating rooms or other equipment. The inventive systems and methods also reduce systemic errors caused by inaccurately positioning reference assemblies on the patient or inaccurately placing a probe tip on a reference assembly as disclosed in U.S. Pat. No. 6,161,032.

The systems and methods described above with reference to FIGS. 4D and 3 also provide more accurate measurements because the reference markers 40d-f inherently move with the patient to enhance the accuracy with which the instrument is positioned relative to the target. For example, the reference markers 40d-f can be implanted very close to soft tissue targets or dynamic organs (e.g., the heart or lungs) so that the reference frame defined by the markers moves with the target. Additionally, because the reference markers and the device markers are located concurrently during a procedure, the dynamic measurement of the reference frame automatically compensates for patient movement. This eliminates having to calibrate the reference frame defined by the markers and having to re-register or re-map images relative to the markers. As a result, the systems and methods described above with reference to FIG. 3 and FIG. 4D provide greater accuracy and enable faster processing times for diagnostic and/or therapeutic procedures.

The systems set forth in FIGS. 3 and 4D further provide additional comfort to the patient throughout the diagnostic and therapeutic procedures. Because the reference markers 40d-f are wireless, they can remain in the patient after implantation for an indefinite period of time without having any leads or markers external to the patient. This allows the patient to go about normal daily functions without complications caused by external lead wires, which is particularly beneficial for treatments that involve one or more procedures over a number of days or weeks. The markers 40d-f, moreover, do not generate a significant amount of heat and they are relatively small. Thus, they do not cause uncomfortable sensations or pain.

E. Methods in Accordance with the System

According to methods of the invention, implanting an electromagnetic marker within in a bone to define a reference point relative to the bone structure; localizing the position of the bone during reconstructive surgery relative to either a prosthesis or another bone structure. According to aspects of the invention, the localization can be in real-time during a procedure with a person in the operating room.

According to further methods of the invention, positioning an electromagnetic marker on a device relative to a bone to define a reference point relative to the bone structure, and the reference point localizes the position of the bone element during reconstructive surgery relative to either a prosthesis or another bone element. In further aspects of this example, the device can have one or more of the following characteristics: the device being a template of known mechanical dimensions temporarily used during surgery; the device being a prosthetic device of known mechanical dimensions and permanently implanted; and/or the device being a bone screw or similar device and permanently implanted.

A method for using implanted an electromagnetic transponder to localize bone components. This method can further include on or more of the following: localization bone components using one or more electromagnetic transponders pre-operatively with X-ray; localization bone components using one or more electromagnetic transponders during surgery electromagnetically; localization bone components using one or more electromagnetic transponders following surgery electromagnetically.

A method for using implanted an electromagnetic transponder to localize bone components relative to prosthetic devices during surgery. According to this method, a marker is directly implanted into the bone of a patient to provide a fixed reference point for use during orthopedic surgery. Alternatively, the marker can be substantially fixed relative to the bony anatomy of a patient to be used as a reference point during orthopedic surgery.

F. Specific Embodiments of Maskers and Localization Systems

The following specific embodiments of markers, excitation sources, sensors and controllers provide additional details to implement the systems and processes described above with reference to FIGS. 1-4C. The present inventors overcame many challenges to develop markers and localization systems that accurately determine the location of a marker which (a) produces a wirelessly transmitted location signal in response to a wirelessly transmitted excitation energy, and (b) has a cross-section small enough to be passed through narrow lumens in the patient. The following specific embodiments are described in sufficient detail to enable a person skilled in the art to make and use such a localization system for tracking catheters and other instruments through the patient, but the invention is not limited to the following embodiments of markers, excitation sources, sensor assemblies and/or controllers.

1. Markers

Figure 5A:
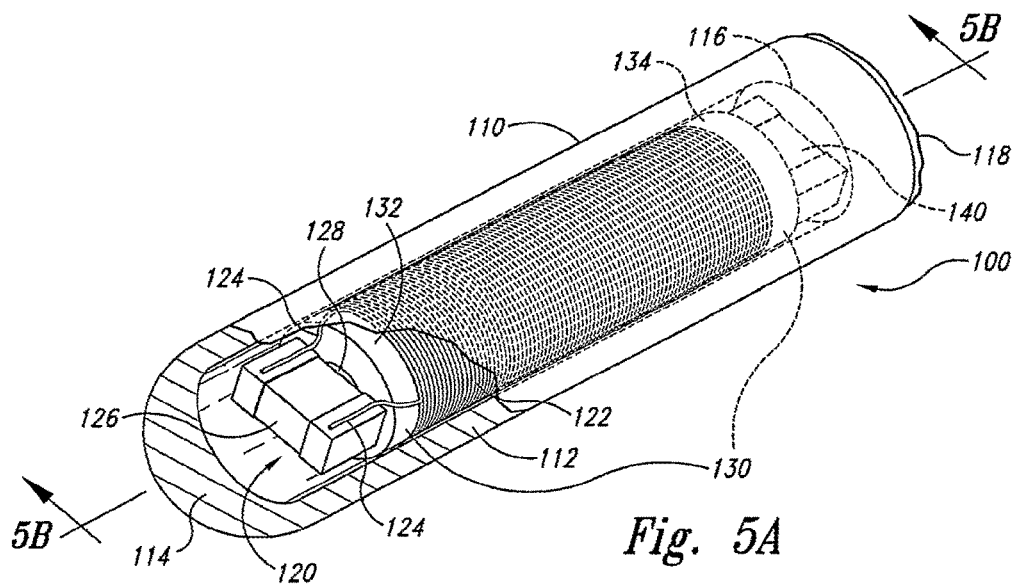
FIG. 5A is an isometric view of a marker for use with an instrument in accordance with an embodiment of the invention.

FIG. 5A is an isometric view of a marker 100 for use with the instrument 10 (FIGS. 1-3). The embodiment of the marker 100 shown in FIG. 5A includes a casing 110 and a magnetic transponder 120 (e.g., a resonating circuit) in the casing 110. The casing 110 is a barrier configured to be implanted in the patient, or attached to the instrument 10 as described above. The casing 110 can alternatively be configured to be adhered to the skin of the patient, or otherwise attached to the patient. The casing 110 can have barbs or other features to anchor the casing 110 in soft tissue or an adhesive for attaching the casing 110 externally to the skin of a patient. Suitable anchoring mechanisms for securing the marker 100 to a patient are disclosed in International Publication No. WO 02/39917 A1, which designates the United States and is incorporated herein by reference. In one embodiment, the casing 110 includes (a) a capsule or shell 112 having a closed end 114 and an open end 116, and (b) a sealant 118 in the open end 116 of the shell 112. The casing 110 and the sealant 118 can be made from plastics, ceramics, glass or other suitable biocompatible materials.

The magnetic transponder 120 can include a resonating circuit that wirelessly transmits a location signal in response to a wirelessly transmitted excitation field as described above. In this embodiment, the magnetic transponder 120 comprises a coil 122 defined by a plurality of windings of a conductor 124. Many embodiments of the magnetic transponder 120 also include a capacitor 126 coupled to the coil 122. The coil 122 resonates at a selected resonant frequency. The coil 122 can resonate at a resonant frequency solely using the parasitic capacitance of the windings without having a capacitor, or the resonant frequency can be produced using the combination of the coil 122 and the capacitor 126. The coil 122 accordingly generates an alternating magnetic field at the selected resonant frequency in response to the excitation energy either by itself or in combination with the capacitor 126. The conductor 124 of the illustrated embodiment can be hot air or alcohol bonded wire having a gauge of approximately 45-52. The coil 122 can have 800-1000 turns, and the windings are preferably wound in a tightly layered coil. The magnetic transponder 120 can further include a core 128 composed of a material having a suitable magnetic permeability. For example, the core 128 can be a ferromagnetic element composed of ferrite or another material. The magnetic transponder 120 can be secured to the casing 110 by an adhesive 129 (FIG. 5B).

The marker 100 also includes an imaging element that enhances the radiographic image of the marker to make the marker more discernible in radiographic images. The imaging element also has a radiographic profile in a radiographic image such that the marker has a radiographic centroid at least approximately coincident with the magnetic centroid of the magnetic transponder 120. As explained in more detail below, the radiographic and magnetic centroids do not need to be exactly coincident with each other, but rather can be within an acceptable range.

Figure 5B:
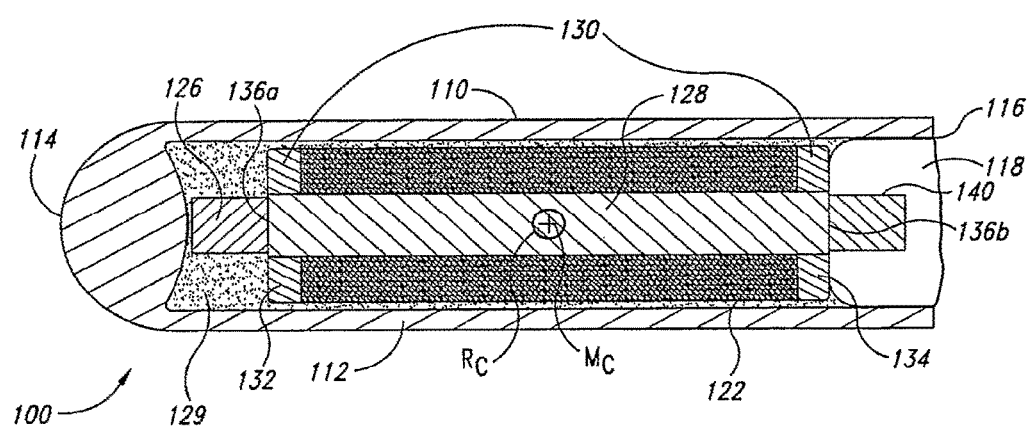
FIG. 5B is a cross-sectional view of the marker of FIG. 5A taken along line 5B-5B.

FIG. 5B is a cross-sectional view of the marker 100 along line 5B-5B of FIG. 5A that illustrates an imaging element 130 in accordance with an embodiment of the invention. The imaging element 130 illustrated in FIGS. 5A-B includes a first contrast element 132 and second contrast element 134. The first and second contrast elements 132 and 134 are generally configured with respect to the magnetic transponder 120 so that the marker 100 has a radiographic centroid Rc that is at least substantially coincident with the magnetic centroid Mc of the magnetic transponder 120. For example, when the imaging element 130 includes two contrast elements, the contrast elements can be arranged symmetrically with respect to the magnetic transponder 120 and/or each other. The contrast elements can also be radiographically distinct from the magnetic transponder 120. In such an embodiment, the symmetrical arrangement of distinct contrast elements enhances the ability to accurately determine the radiographic centroid of the marker 100 in a radiographic image.

The first and second contrast elements 132 and 134 illustrated in FIGS. 5A-B are continuous rings positioned at opposing ends of the core 128. The first contrast element 132 can be at or around a first end 136a of the core 128, and the second contrast element 134 can be at or around a second end 136b of the core 128. The continuous rings shown in FIGS. 5A-B have substantially the same diameter and thickness. The first and second contrast elements 132 and 134, however, can have other configurations and/or be in other locations relative to the core 128 in other embodiments. For example, the first and second contrast elements 132 and 134 can be rings with different diameters and/or thicknesses.

The radiographic centroid of the image produced by the imaging element 130 does not need to be absolutely coincident with the magnetic centroid Mc, but rather the radiographic centroid and the magnetic centroid should be within an acceptable range. For example, the radiographic centroid Rc can be considered to be at least approximately coincident with the magnetic centroid Mc when the offset between the centroids is less than approximately 5 mm. In more stringent applications, the magnetic centroid Mc and the radiographic centroid Rc are considered to be at least substantially coincident with each other when the offset between the centroids is 2 mm or less. In other applications, the magnetic centroid Mc is at least approximately coincident with the radiographic centroid Rc when the centroids are spaced apart by a distance not greater than half the length of the magnetic transponder 120 and/or the marker 100.

The imaging element 130 can be made from a material and configured appropriately to absorb a high fraction of incident photons of a radiation beam used for producing the radiographic image. For example, when the imaging radiation has high-acceleration voltages in the megavoltage range, the imaging element 130 is made from, at least in part, high-density materials with sufficient thickness and cross-sectional area to absorb enough of the photon fluence incident on the imaging element to be visible in the resulting radiograph. Many high-energy beams used for therapy have acceleration voltages of 6 MV-25 MV, and these beams are often used to produce radiographic images in the 5 MV-10 MV range, or more specifically in the 6 MV-8 MV range. As such, the imaging element 130 can be made from a material that is sufficiently absorbent of incident photon fluence to be visible in an image produced using a beam with an acceleration voltage of 5 MV-10 MV, or more specifically an acceleration voltage of 6 MV-8 MV.

Several specific embodiments of imaging elements 130 can be made from gold, tungsten, platinum and/or other high-density metals. In these embodiments the imaging element 130 can be composed of materials having a density of 19.25 g/cm3 (density of tungsten) and/or a density of approximately 21.4 g/cm3 (density of platinum). Many embodiments of the imaging element 130 accordingly have a density not less than 19 g/cm3. In other embodiments, however, the material(s) of the imaging element 130 can have a substantially lower density. For example, imaging elements with lower-density materials are suitable for applications that use lower-energy radiation to produce radiographic images. Moreover, the first and second contrast elements 132 and 134 can be composed of different materials such that the first contrast element 132 can be made from a first material and the second contrast element 134 can be made from a second material.

Referring to FIG. 5B, the marker 100 can further include a module 140 at an opposite end of the core 128 from the capacitor 126. In the embodiment of the marker 100 shown in FIG. 5B, the module 140 is configured to be symmetrical with respect to the capacitor 126 to enhance the symmetry of the radiographic image. As with the first and second contrast elements 132 and 134, the module 140 and the capacitor 126 are arranged such that the magnetic centroid of the marker 100 is at least approximately coincident with the radiographic centroid of the marker 100. The module 140 can be another capacitor that is identical to the capacitor 126, or the module 140 can be an electrically inactive element. Suitable electrically inactive modules include ceramic blocks shaped like the capacitor 126 and located with respect to the coil 122, the core 128 and the imaging element 130 to be symmetrical with each other. In still other embodiments the module 140 can be a different type of electrically active element electrically coupled to the magnetic transponder 120.

One specific process of using the marker involves imaging the marker using a first modality and then tracking the target of the patient and/or the marker using a second modality. For example, the location of the marker relative to the target can be determined by imaging the marker and the target using radiation. The marker and/or the target can then be localized and tracked using the magnetic field generated by the marker in response to an excitation energy in a non-ionizing environment.

Figure 5C:
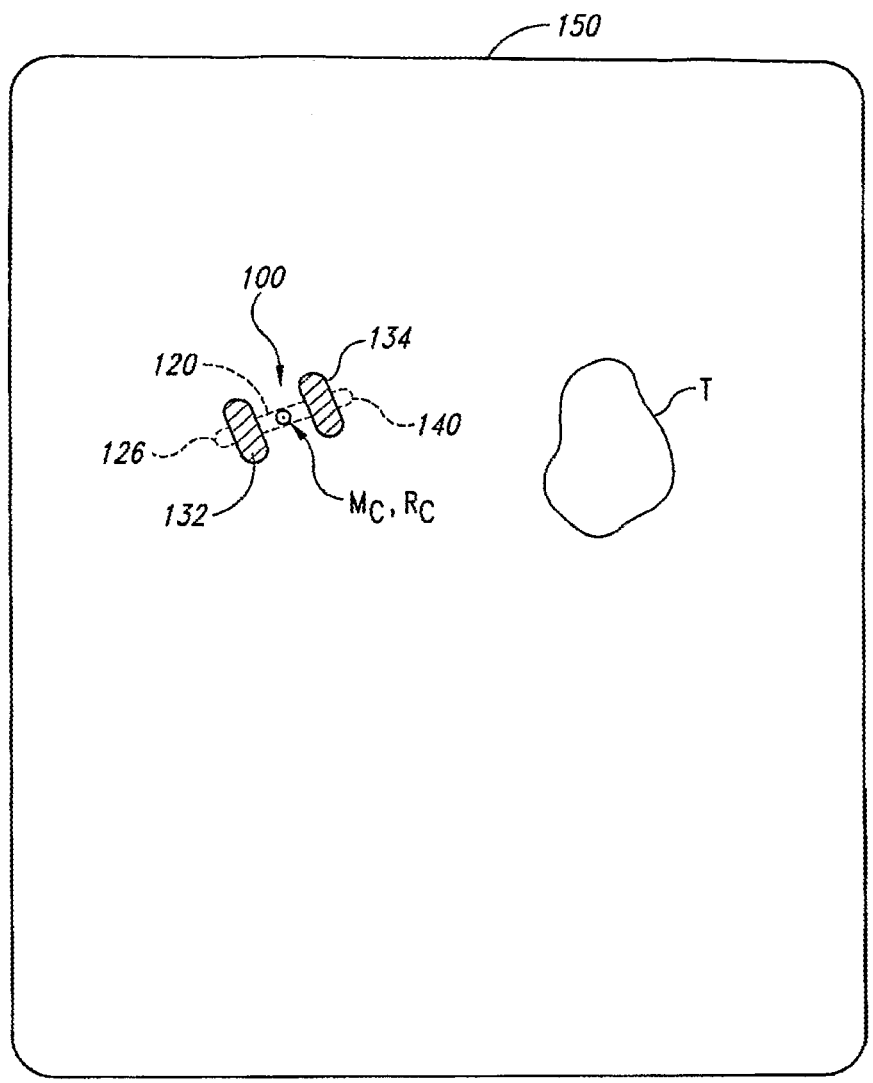
FIG. 5C is an illustration of a radiographic image of the marker of FIGS. 5A-B.

The marker 100 shown in FIGS. 5A-B is expected to provide an enhanced radiographic image compared to conventional magnetic markers for more accurately determining the relative position between the marker and the target of a patient. FIG. 5C, for example, illustrates a radiographic image 150 of the marker 100 and a target T of the patient. The first and second contrast elements 132 and 134 are expected to be more distinct in the radiographic image 150 because they can be composed of higher density materials than the components of the magnetic transponder 120. The first and second contrast elements 132 and 134 can accordingly appear as bulbous ends of a dumbbell shape in applications in which the components of the magnetic transponder 120 are visible in the image. In certain megavolt applications, the components of the magnetic transponder 120 may not appear at all on the radiographic image 150 such that the first and second contrast elements 132 and 134 will appear as distinct regions that are separate from each other. In either embodiment, the first and second contrast elements 132 and 134 provide a reference frame in which the radiographic centroid Rc of the marker 100 can be located in the image 150. Moreover, because the imaging element 130 is configured so that the radiographic centroid Rc is at least approximately coincident with the magnetic centroid Mc, the relative offset or position between the target T and the magnetic centroid Mc can be accurately determined using the marker 100. The embodiment of the marker 100 illustrated in FIGS. 5A-C, therefore, is expected to mitigate errors caused by incorrectly estimating the radiographic and magnetic centroids of markers in radiographic images.

Figure 6A:
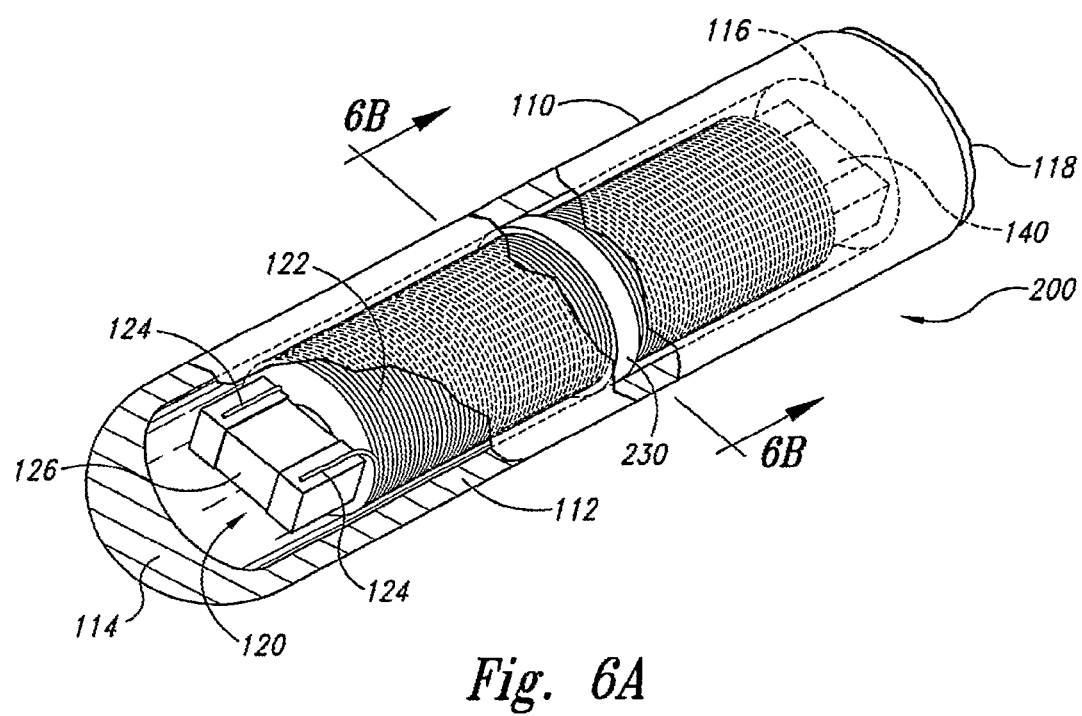
FIG. 6A is an isometric view of a marker for use with an instrument in accordance with another embodiment of the invention.
Figure 6B:
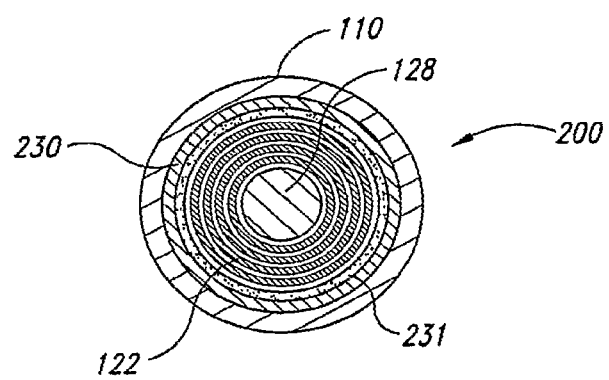
FIG. 6B is a cross-sectional view of the marker of FIG. 6A taken along line 6B-6B.

FIG. 6A is an isometric view of a marker 200 with a cutaway portion to illustrate internal components, and FIG. 6B is a cross-sectional view of the marker 200 taken along line 6B-6B of FIG. 6A. The marker 200 is similar to the marker 100 shown above in FIG. 5A, and thus like reference numbers refer to like components. The marker 200 differs from the marker 100 in that the marker 200 includes an imaging element 230 defined by a single contrast element. The imaging element 230 is generally configured relative to the magnetic transponder 120 so that the radiographic centroid of the marker 200 is at least approximately coincident with the magnetic centroid of the magnetic transponder 120. The imaging element 230, more specifically, is a ring extending around the coil 122 at a medial region of the magnetic transponder 120. The imaging element 230 can be composed of the same materials described above with respect to the imaging element 130 in FIGS. 5A-B. The imaging element 230 can have an inner diameter approximately equal to the outer diameter of the coil 122, and an outer diameter within the casing 110. As shown in FIG. 6B, however, a spacer 231 can be between the inner diameter of the imaging element 230 and the outer diameter of the coil 122.

The marker 200 is expected to operate in a manner similar to the marker 100 described above. The marker 200, however, does not have two separate contrast elements that provide two distinct, separate points in a radiographic image. The imaging element 230 is still highly useful in that it identifies the radiographic centroid of the marker 200 in a radiographic image, and it can be configured so that the radiographic centroid of the marker 200 is at least approximately coincident with the magnetic centroid of the magnetic transponder 120.

Figure 7A:
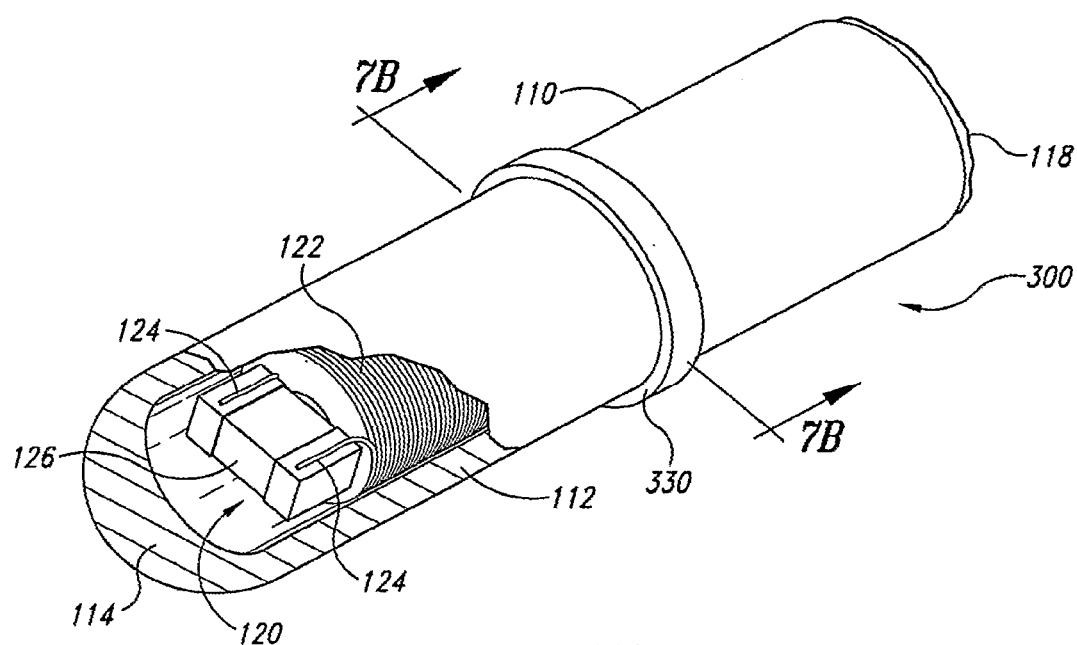
FIG. 7A is an isometric view of a marker for use with an instrument in accordance with another embodiment of the invention.
Figure 7B:
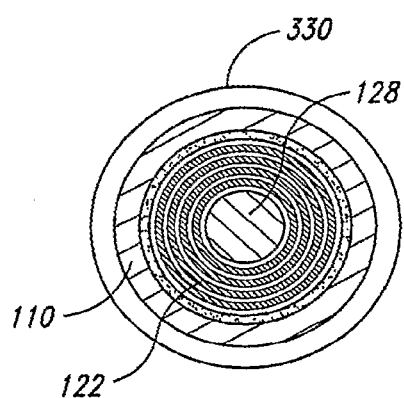
FIG. 7B is a cross-sectional view of the marker of FIG. 7A taken along line 7B-7B.

FIG. 7A is an isometric view of a marker 300 with a cutaway portion, and FIG. 7B is a cross-sectional view of the marker 300 taken along line 7B-7B of FIG. 7A. The marker 300 is substantially similar to the marker 200 shown in FIGS. 6A-B, and thus like reference numbers refer to like components in FIGS. 5A-7B. The imaging element 330 can be a high-density ring configured relative to the magnetic transponder 120 so that the radiographic centroid of the marker 300 is at least approximately coincident with the magnetic centroid of the magnetic transponder 120. The marker 300, more specifically, includes an imaging element 330 around the casing 110. The marker 300 is expected to operate in much the same manner as the marker 200 shown in FIGS. 6A-B.

Figure 8:
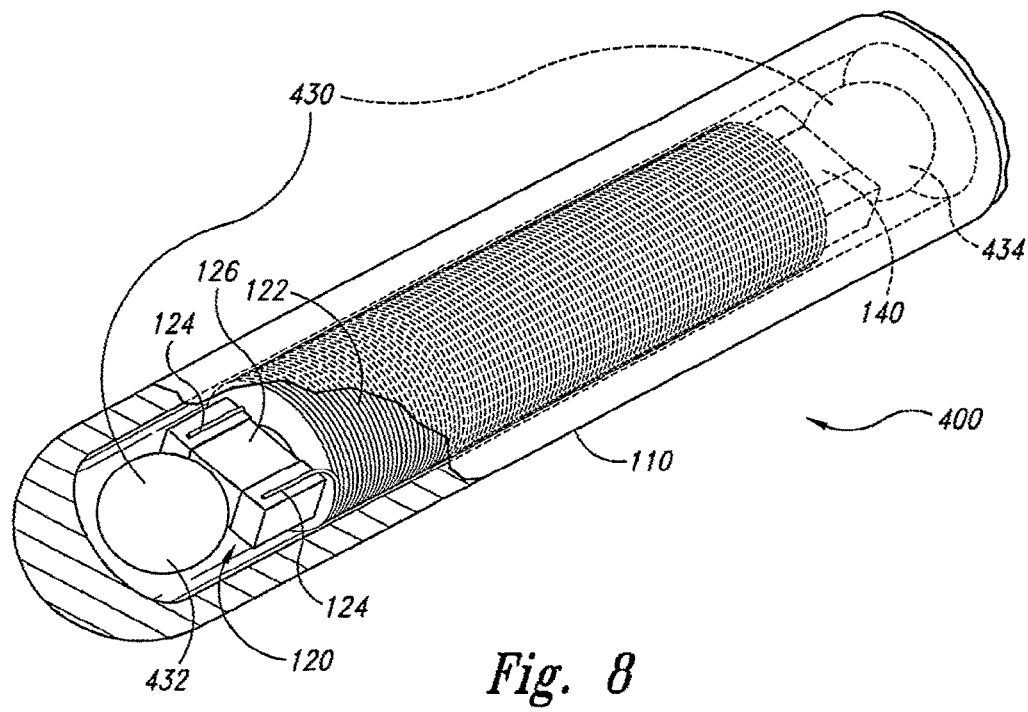
FIG. 8 is an isometric view of a marker for use with an instrument in accordance with another embodiment of the invention.

FIG. 8 is an isometric view with a cutaway portion illustrating a marker 400 in accordance with another embodiment of the invention. The marker 400 is similar to the marker 100 shown in FIGS. 5A-C, and thus like reference numbers refer to like components in these Figures. The marker 400 has an imaging element 430 including a first contrast element 432 at one end of the magnetic transponder 120 and a second contrast element 434 at another end of the magnetic transponder 120. The first and second contrast elements 432 and 434 are spheres composed of suitable high-density materials. The contrast elements 432 and 434, for example, can be composed of gold, tungsten, platinum or other suitable high-density materials for use in radiographic imaging. The marker 400 is expected to operate in a manner similar to the marker 100, as described above.

Figure 9:
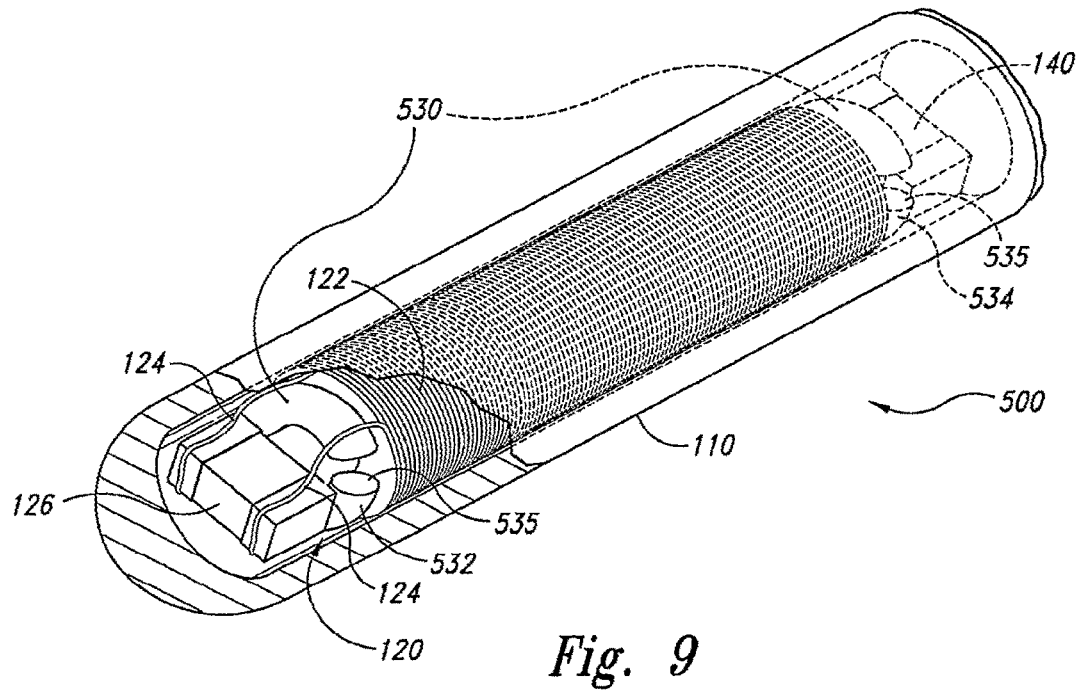
FIG. 9 is an isometric view of a marker for use with an instrument in accordance with yet another embodiment of the invention.

FIG. 9 is an isometric view with a cutaway portion of a marker 500 in accordance with yet another embodiment of the invention. The marker 500 is substantially similar to the markers 100 and 400 shown in FIGS. 5A and 8, and thus like reference numbers refer to like components in these Figures. The marker 500 includes an imaging element 530 including a first contrast element 532 and a second contrast element 534. The first and second contrast elements 532 and 534 can be positioned proximate to opposing ends of the magnetic transponder 120. The first and second contrast elements 532 and 534 can be discontinuous rings having a gap 535 to mitigate eddy currents. The contrast elements 532 and 534 can be composed of the same materials as described above with respect to the contrast elements of other imaging elements in accordance with other embodiments of the invention.

Additional embodiments of markers in accordance with the invention can include imaging elements incorporated into or otherwise integrated with the casing 110, the core 128 (FIG. 5B) of the magnetic transponder 120, and/or the adhesive 129 (FIG. 5B) in the casing. For example, particles of a high-density material can be mixed with ferrite and extruded to form the core 128. Alternative embodiments can mix particles of a high-density material with glass or another material to form the casing 110, or coat the casing 110 with a high-density material. In still other embodiments, a high-density material can be mixed with the adhesive 129 and injected into the casing 110. Any of these embodiments can incorporate the high-density material into a combination of the casing 110, the core 128 and/or the adhesive 129. Suitable high-density materials can include tungsten, gold and/or platinum as described above.

The markers described above with reference to FIGS. 5A-9 can be used for the markers 40 in the instrument 10 (FIGS. 1-4C). The instrument 10 can have several markers with the same type of imaging elements, or markers with different imaging elements can be used with the same instrument. Several additional details of these markers and other embodiments of markers are described in U.S. application Ser. Nos. 10/334,698 and 10/746,888, which are incorporated herein by reference. For example, the markers may not have any imaging elements for applications with lower-energy radiation, or the markers may have reduced volumes of ferrite and metals to mitigate issues with MRI imaging as set forth in U.S. application Ser. No. 10/334,698.

2. Localization Systems

Figure 10:
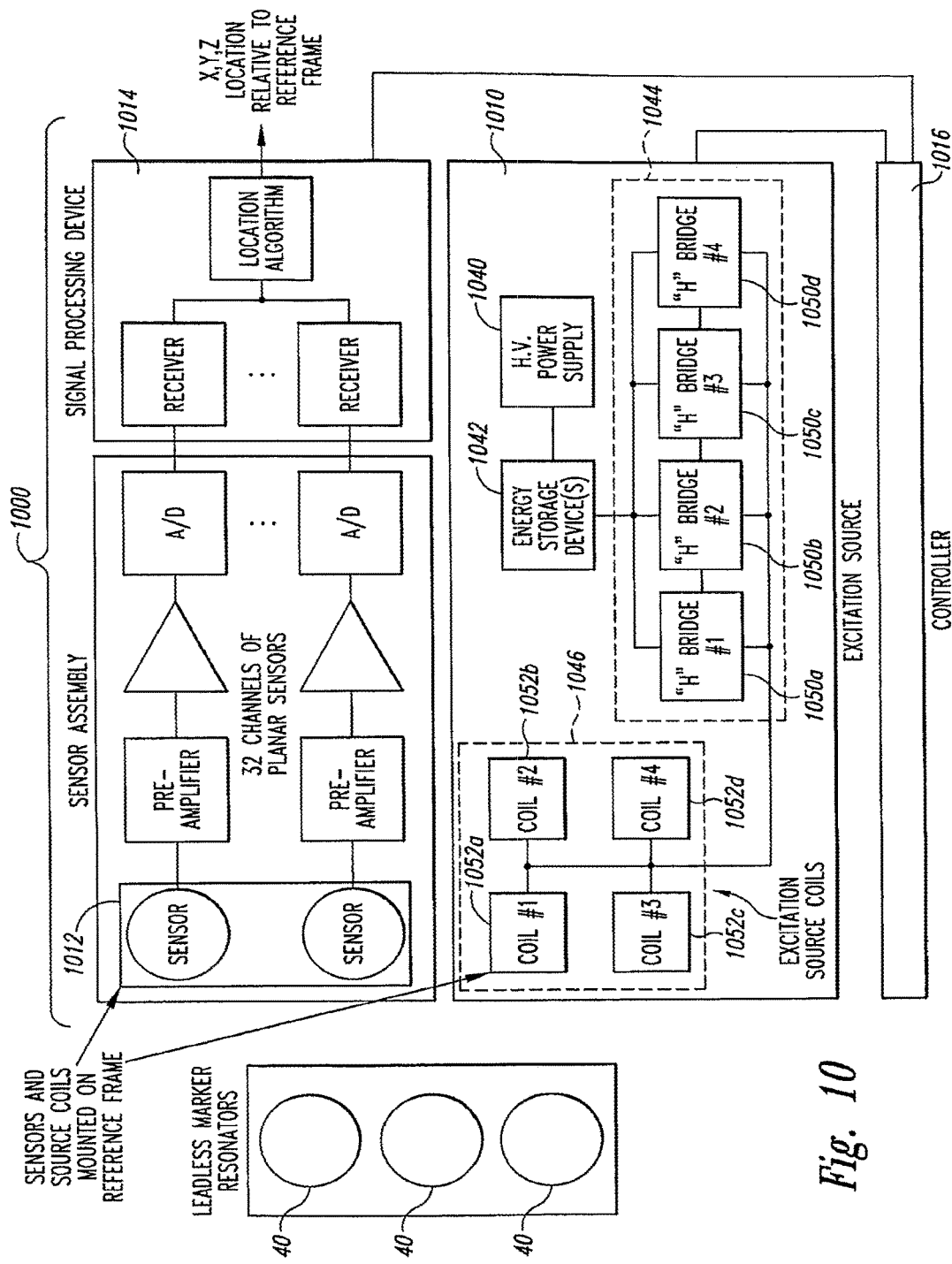
FIG. 10 is a schematic block diagram of a localization system for use in locating an instrument in accordance with an embodiment of the invention.

FIG. 10 is a schematic block diagram of a localization system 1000 for determining the absolute location of the markers 40 (shown schematically) relative to a reference frame. The localization system 1000 includes an excitation source 1010, a sensor assembly 1012, a signal processor 1014 operatively coupled to the sensor assembly 1012, and a controller 1016 operatively coupled to the excitation source 1010 and the signal processor 1014. The excitation source 1010 is one embodiment of the excitation source 60 described above with reference to FIG. 4A; the sensor assembly 1012 is one embodiment of the sensor assembly 70 described above with reference to FIG. 4A; and the controller 1016 is one embodiment of the controller 80 described above with reference to FIG. 4A.

The excitation source 1010 is adjustable to generate a magnetic field having a waveform with energy at selected frequencies to match the resonant frequencies of the markers 40. The magnetic field generated by the excitation source 1010 energizes the markers at their respective frequencies. After the markers 40 have been energized, the excitation source 1010 is momentarily switched to an "off" position so that the pulsed magnetic excitation field is terminated while the markers wirelessly transmit the location signals. This allows the sensor assembly 1012 to sense the location signals from the markers 40 without measurable interference from the significantly more powerful magnetic field from the excitation source 1010. The excitation source 1010 accordingly allows the sensor assembly 1012 to measure the location signals from the markers 40 at a sufficient signal-to-noise ratio so that the signal processor 1014 or the controller 1016 can accurately calculate the absolute location of the markers 40 relative to a reference frame.

a. Excitation Sources

Referring still to FIG. 10, the excitation source 1010 includes a high-voltage power supply 1040, an energy storage device 1042 coupled to the power supply 1040, and a switching network 1044 coupled to the energy storage device 1042. The excitation source 1010 also includes a coil assembly 1046 coupled to the switching network 1044. In one embodiment, the power supply 1040 is a 500 volt power supply, although other power supplies with higher or lower voltages can be used. The energy storage device 1042 in one embodiment is a high-voltage capacitor that can be charged and maintained at a relatively constant charge by the power supply 1040. The energy storage device 1042 alternately provides energy to and receives energy from the coils in the coil assembly 1046.

The energy storage device 1042 is capable of storing adequate energy to reduce voltage drop in the energy storage device while having a low series resistance to reduce power losses. The energy storage device 1042 also has a low series inductance to more effectively drive the coil assembly 1046. Suitable capacitors for the energy storage device 1042 include aluminum electrolytic capacitors used in flash energy applications. Alternative energy storage devices can also include NiCd and lead acid batteries, as well as alternative capacitor types, such as tantalum, film, or the like.

The switching network 1044 includes individual H-bridge switches 1050 (identified individually by reference numbers 1050a-d), and the coil assembly 1046 includes individual source coils 1052 (identified individually by reference numbers 1052a-d). Each H-bridge switch 1050 controls the energy flow between the energy storage device 1042 and one of the source coils 1052. For example, H-bridge switch #1 1050a independently controls the flow of the energy to/from source coil #1 1052a, H-bridge switch #2 1050b independently controls the flow of the energy to/from source coil #2 1052b, H-bridge switch #3 1050c independently controls the flow of the energy to/from source coil #3 1052c, and H-bridge switch #4 1050d independently controls the flow of the energy to/from source coil #4 1052d. The switching network 1044 accordingly controls the phase of the magnetic field generated by each of the source coils 1052a-d independently. The H-bridges 1050 can be configured so that the electrical signals for all the source coils 1052 are in phase, or the H-bridges 1050 can be configured so that one or more of the source coils 1052 are 180° out of phase. Furthermore, the H-bridge switches 1050 can be configured so that the electrical signals for one or more of the source coils 1052 are between 0 and 180° out of phase to simultaneously provide magnetic fields with different phases.

The source coils 1052 can be arranged in a coplanar array fixed relative to the reference frame. Each source coil 1052 can be a square, planar winding arranged to form a flat, substantially rectilinear coil. The source coils 1052 can have other shapes and other configurations in different embodiments. In one embodiment, the source coils 1052 are individual conductive lines formed in a stratum of a printed circuit board, or windings of a wire in a foam frame. Alternatively, the source coils 1052 can be formed in different substrates or arranged so that two or more of the source coils are not planar with each other. Additionally, alternate embodiments of the invention may have fewer or more source coils than illustrated in FIG. 10.

The selected magnetic fields from the source coils 1052 combine to form an adjustable excitation field that can have different three-dimensional shapes to excite the markers 40 at any spatial orientation within an excitation volume. When the planar array of the source coils 1052 is generally horizontal, the excitation volume is positioned above an area approximately corresponding to the central region of the coil assembly 1046. The excitation volume is the three-dimensional space adjacent to the coil assembly 1046 in which the strength of the magnetic field is sufficient to adequately energize the markers 40.

Figure 11:
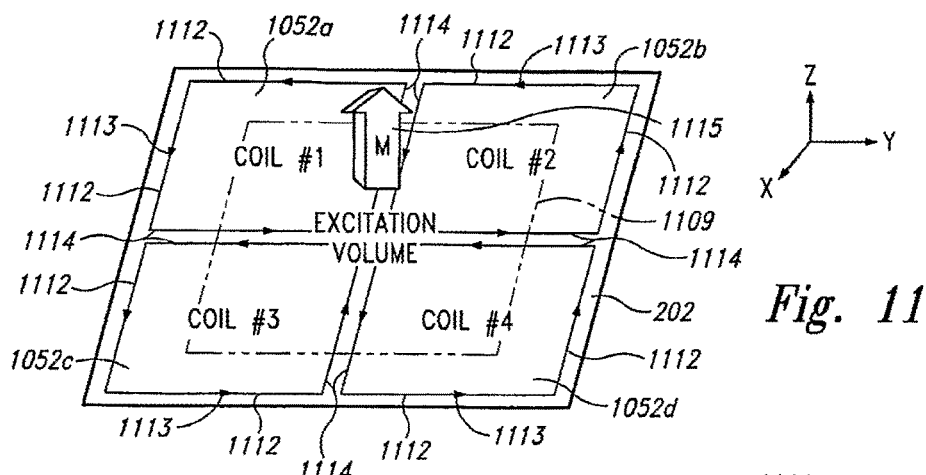
FIG. 11 is a schematic view of an array of coplanar source coils carrying electrical signals in a first combination of phases to generate a first excitation field.
Figure 12:
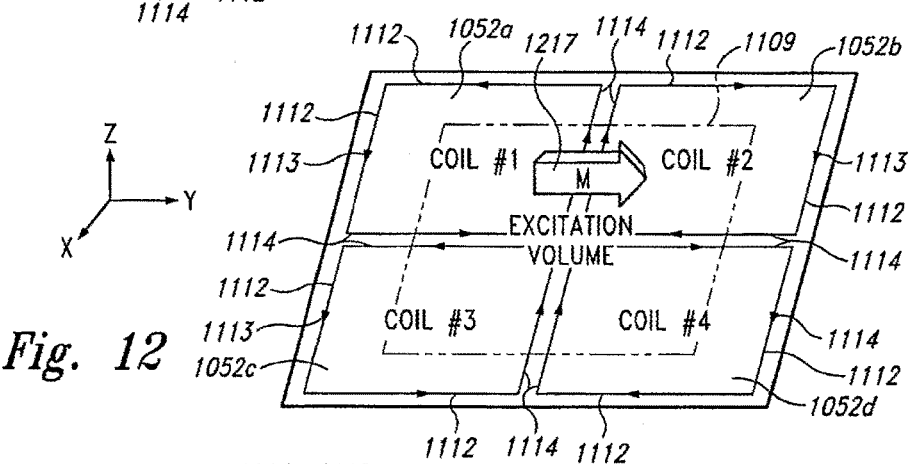
FIG. 12 is a schematic view of an array of coplanar source coils carrying electrical signals in a second combination of phases to generate a second excitation field.
Figure 13:
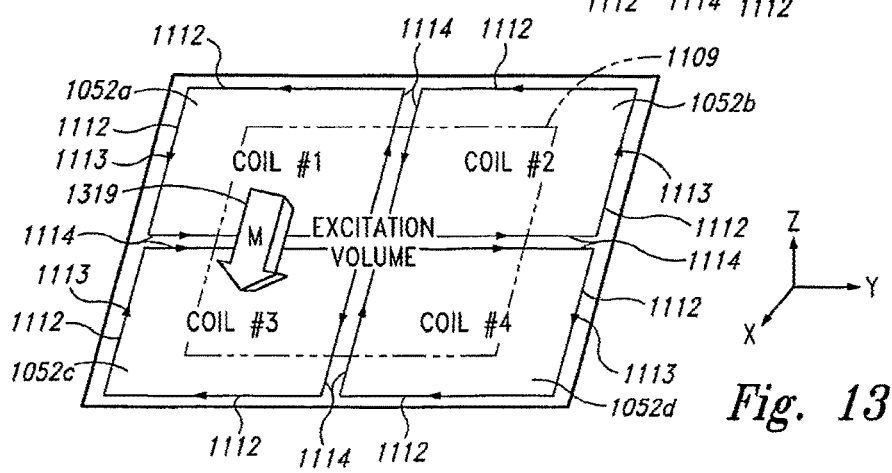
FIG. 13 is a schematic view of an array of coplanar source coils carrying electrical signals in a third combination of phases to generate a third excitation field.

FIGS. 11-13 are schematic views of a planar array of the source coils 1052 with the alternating electrical signals provided to the source coils in different combinations of phases to generate excitation fields about different axes relative to the illustrated XYZ coordinate system. Each source coil 1052 has two outer sides 1112 and two inner sides 1114. Each inner side 1114 of one source coil 1052 is immediately adjacent to an inner side 1114 of another source coil 1052, but the outer sides 1112 of all the source coils 1052 are not adjacent to any other source coil 1052.

In the embodiment of FIG. 11, all the source coils 1052a-d simultaneously receive alternating electrical signals in the same phase. As a result, the electrical current flows in the same direction through all the source coils 1052a-d such that a direction 1113 of the current flowing along the inner sides 1114 of one source coil (e.g., source coil 1052a) is opposite to the direction 1113 of the current flowing along the inner sides 1114 of the two adjacent source coils (e.g., source coils 1052c and 1052d). The magnetic fields generated along the inner sides 1114 accordingly cancel each other out so that the magnetic field is effectively generated from the current flowing along the outer sides 1112 of the source coils. The resulting excitation field formed by the combination of the magnetic fields from the source coils 1052a-d shown in FIG. 11 has a magnetic moment 1115 generally in the Z direction within an excitation volume 1109. This excitation field energizes markers parallel to the Z-axis or markers positioned with an angular component along the Z-axis (i.e., not orthogonal to the Z-axis).

FIG. 12 is a schematic view of the source coils 1052a-d with the alternating electrical signals provided in a second combination of phases to generate a second excitation field with a different spatial orientation. In this embodiment, source coils 1052a and 1052c are in phase with each other, and source coils 1052b and 1052d are in phase with each other. However, source coils 1052a and 1052c are 180 degrees out of phase with source coils 1052b and 1052d. The magnetic fields from the source coils 1052a-d combine to generate an excitation field having a magnetic moment 1217 generally in the Y direction within the excitation volume 1109. Accordingly, this excitation field energizes markers parallel to the Y-axis or markers positioned with an angular component along the Y-axis.

FIG. 13 is a schematic view of the source coils 1052a-d with the alternating electrical signals provided in a third combination of phases to generate a third excitation field with a different spatial orientation. In this embodiment, source coils 1052a and 1052b are in phase with each other, and source coils 1052c and 1052d are in phase with each other. However, source coils 1052a and 1052b are 180 degrees out of phase with source coils 1052c and 1052d. The magnetic fields from the source coils 1052a-d combine to generate an excitation field having a magnetic moment 1319 in the excitation volume 1109 generally in the direction of the X-axis. Accordingly, this excitation field energizes markers parallel to the X-axis or markers positioned with an angular component along the X-axis.

Figure 14:
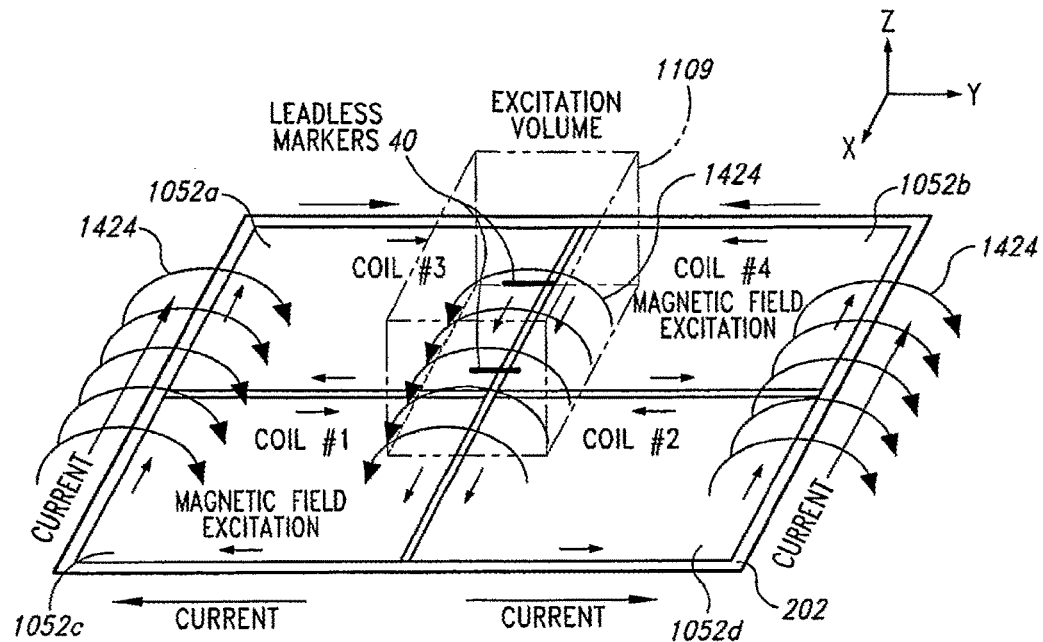
FIG. 14 is a schematic view of an array of coplanar source coils illustrating a magnetic excitation field for energizing markers in a first spatial orientation.

FIG. 14 is a schematic view of the source coils 1052a-d illustrating the current flow to generate an excitation field 1424 for energizing markers 40 with longitudinal axes parallel to the Y-axis. The switching network 1044 (FIG. 10) is configured so that the phases of the alternating electrical signals provided to the source coils 1052a-d are similar to the configuration of FIG. 12. This generates the excitation field 1424 with a magnetic moment in the Y direction to energize the markers 40.

Figure 15:
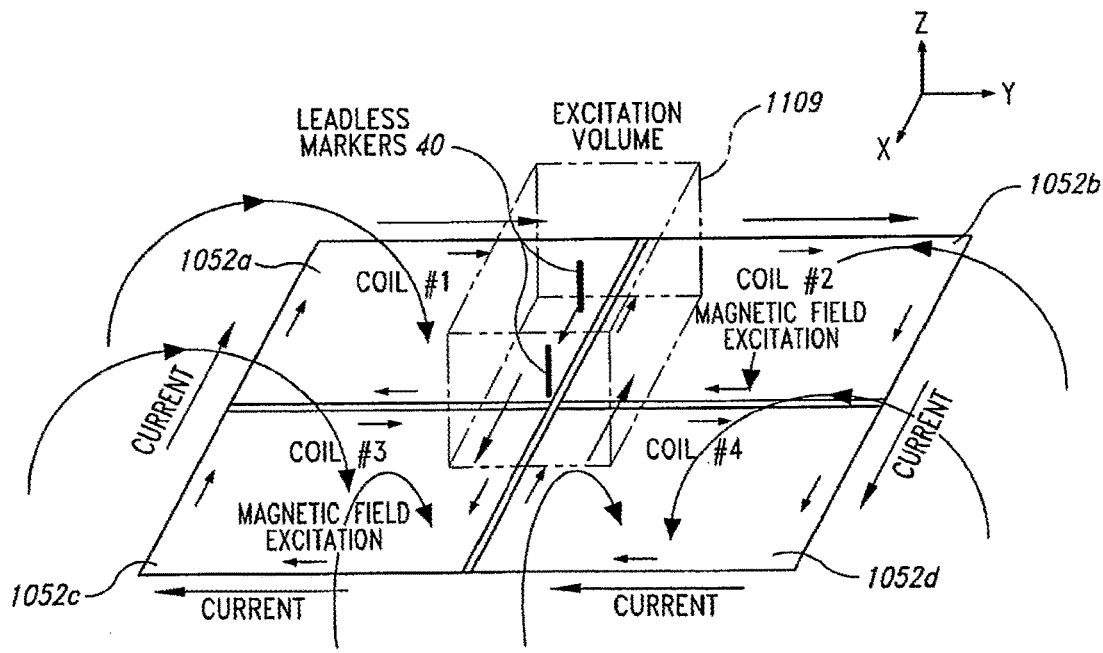
FIG. 15 is a schematic view of an array of coplanar source coils illustrating a magnetic excitation field for energizing markers in a second spatial orientation.

FIG. 15 further illustrates the ability to spatially adjust the excitation field in a manner that energizes any of the markers 40 at different spatial orientations. In this embodiment, the switching network 1044 (FIG. 10) is configured so that the phases of the alternating electrical signals provided to the source coils 1052a-d are similar to the configuration shown in FIG. 11. This produces an excitation field with a magnetic moment in the Z direction that energizes markers 40 with longitudinal axes parallel to the Z-axis.

The spatial configuration of the excitation field in the excitation volume 1109 can be quickly adjusted by manipulating the switching network to change the phases of the electrical signals provided to the source coils 1052a-d. As a result, the overall magnetic excitation field can be changed to be oriented in either the X, Y or Z directions within the excitation volume 1109. This adjustment of the spatial orientation of the excitation field reduces or eliminates blind spots in the excitation volume 1109. Therefore, the markers 40 within the excitation volume 1109 can be energized by the source coils 1052a-d regardless of the spatial orientations of the leadless markers.

In one embodiment, the excitation source 1010 is coupled to the sensor assembly 1012 so that the switching network 1044 (FIG. 10) adjusts orientation of the pulsed generation of the excitation field along the X, Y, and Z axes depending upon the strength of the signal received by the sensor assembly 1012. If the location signal from a marker 40 is insufficient, the switching network 1044 can automatically change the spatial orientation of the excitation field during a subsequent pulsing of the source coils 1052a-d to generate an excitation field with a moment in the direction of a different axis or between axes. The switching network 1044 can be manipulated until the sensor assembly 1012 receives a sufficient location signal from the marker.

The excitation source 1010 illustrated in FIG. 10 alternately energizes the source coils 1052a-d during an excitation phase to power the markers 40, and then actively de-energizes the source coils 1052a-d during a sensing phase in which the sensor assembly 1012 senses the decaying location signals wirelessly transmitted by the markers 40. To actively energize and de-energize the source coils 1052a-d, the switching network 1044 is configured to alternatively transfer stored energy from the energy storage device 1042 to the source coils 1052a-d, and to then "re-transfer" energy from the source coils 1052a-d back to the energy storage device 1042. The switching network 1044 alternates between first and second "on" positions so that the voltage across the source coils 1052 alternates between positive and negative polarities. For example, when the switching network 1044 is switched to the first on position, the energy in the energy storage device 1042 flows to the source coils 1052a-d. When the switching network 1044 is switched to the second "on" position, the polarity is reversed such that the energy in the source coils 1052a-d is actively drawn from the source coils 1052a-d and directed back to the energy storage device 1042. As a result, the energy in the source coils 1052a-d is quickly transferred back to the energy storage device 1042 to abruptly terminate the excitation field transmitted from the source coils 1052a-d and to conserve power consumed by the energy storage device 1042. This removes the excitation energy from the environment so that the sensor assembly 1012 can sense the location signals from the markers 40 without interference from the significantly larger excitation energy from the excitation source 1010. Several additional details of the excitation source 1010 and alternate embodiments are disclosed in U.S. patent application Ser. No. 10/213,980 filed on Aug. 7, 2002, which is incorporated by reference herein in its entirety.

b. Sensor Assemblies

Figure 16A:
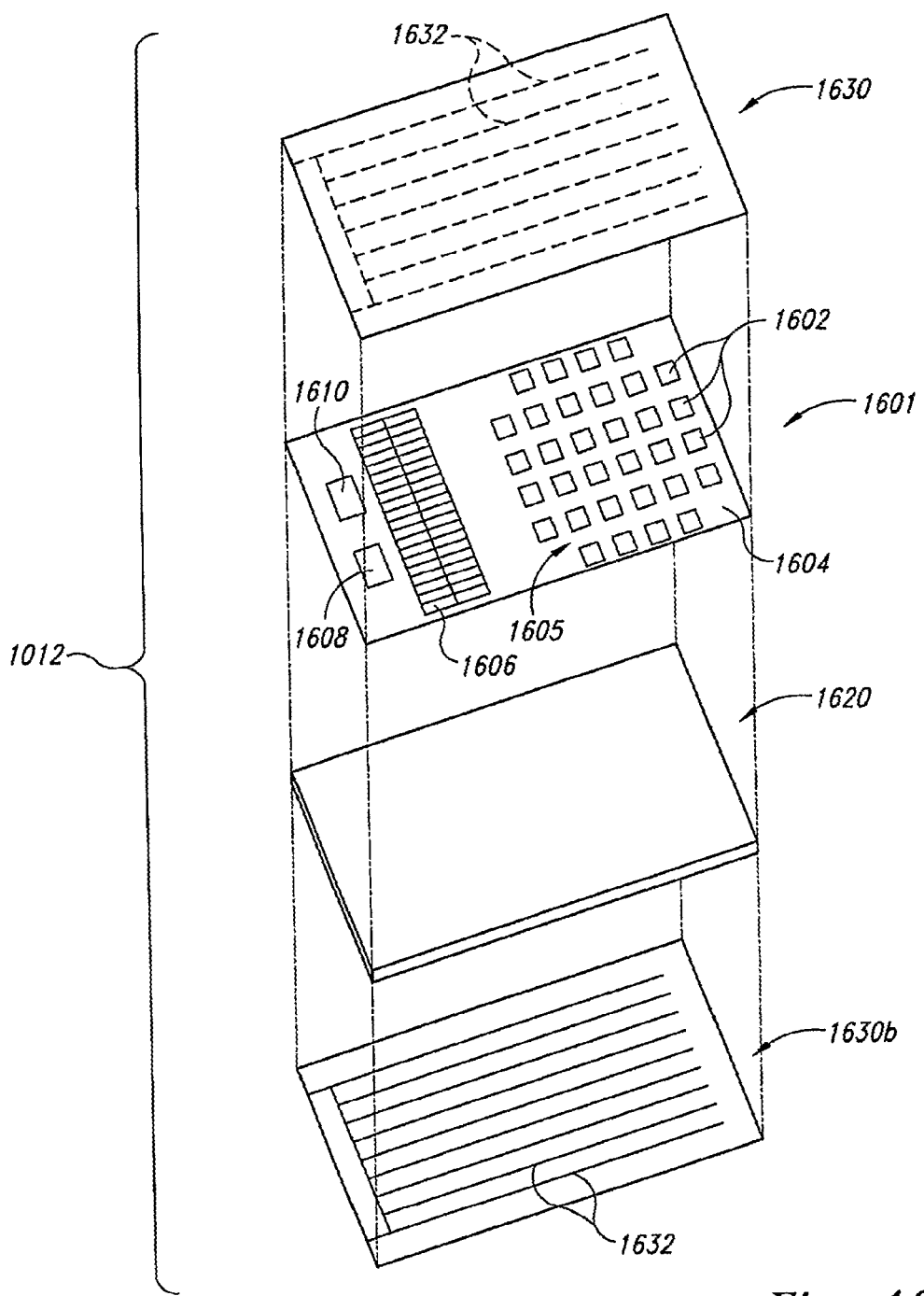
FIG. 16A is an exploded isometric view showing individual components of a sensor assembly for use with a localization system to localize an instrument in accordance with an embodiment of the invention.

FIG. 16A is an exploded isometric view showing several components of the sensor assembly 1012 for use in the localization system 1000 (FIG. 10). The sensor assembly 1012 includes a sensing unit 1601 having a plurality of coils 1602 formed on or carried by a panel 1604. The coils 1602 can be field sensors or magnetic flux sensors arranged in a sensor array 1605.

The panel 1604 may be a substantially nonconductive material, such as a sheet of KAPTON® produced by DuPont. KAPTON® is particularly useful when an extremely stable, tough, and thin film is required (such as to avoid radiation beam contamination), but the panel 1604 may be made from other materials and have other configurations. For example, FR4 (epoxy-glass substrates), GETEK or other Teflon-based substrates, and other commercially available materials can be used for the panel 1604. Additionally, although the panel 1604 may be a flat, highly planar structure, in other embodiments, the panel may be curved along at least one axis. In either embodiment, the field sensors (e.g., coils) are arranged in a locally planar array in which the plane of one field sensor is at least substantially coplanar with the planes of adjacent field sensors. For example, the angle between the plane defined by one coil relative to the planes defined by adjacent coils can be from approximately 0° to 10°, and more generally is less than 5°. In some circumstances, however, one or more of the coils may be at an angle greater than 10° relative to other coils in the array.

The sensor assembly 1012 shown in FIG. 16A can optionally include a core 1620 laminated to the panel 1604. The core 1620 can be a support member made from a rigid material, or the core 1620 can be a low-density foam (e.g., closed-cell Rohacell foam). The core 1620 is preferably a stable layer that has a low coefficient of thermal expansion so that the shape of the sensor assembly 1012 and the relative orientation between the coils 1602 remain within a defined range over an operating temperature range.

The sensor assembly 1012 can further include a first exterior cover 1630*a* on one side of the sensing subsystem and a second exterior cover 1630*b* on an opposing side. The first and second exterior covers 1630*a-b* can be thin, thermally stable layers, such as Kevlar or Thermount films. Each of the first and second exterior covers 1630*a-b* can include electric shielding 1632 to block undesirable external electric fields from reaching the coils 1602. The electric shielding 1632, for example, prevents or minimizes the presence of eddy currents caused by the coils 1602 or external magnetic fields. The electric shielding 1632 can be a plurality of parallel legs of gold-plated copper strips to define a comb-shaped shield in a configuration commonly called a Faraday shield. It will be appreciated that the electrical shielding 1632 can be formed from other materials that are suitable for shielding. The electric shielding 1632 can be formed on the first and second exterior covers 1630*a-b* using printed circuit board manufacturing technology or other techniques.

The panel 1604 with the coils 1602 is laminated to the core 1620 using a pressure sensitive adhesive or another type of adhesive. The first and second exterior covers 1630*a-b* are similarly laminated to the assembly of the panel 1604 and the core 1620. The laminated assembly forms a rigid structure that fixedly retains the arrangement of the coils 1602 in a defined configuration over a large operating temperature range. As such, the sensor assembly 1012 does not substantially deflect across its surface during operation. The sensor assembly 1012, for example, can retain the array of coils 1602 in the fixed position with a deflection of no greater than ±0.5 mm, and in some cases no more than ±0.3 mm. The stiffness of the sensing subsystem provides very accurate and repeatable monitoring of the precise location of leadless markers in real time.

In still another embodiment, the sensor assembly 1012 can further include a plurality of source coils that are a component of the excitation source 1010. One suitable array combining the sensor assembly 1012 with source coils is disclosed in U.S. patent application Ser. No. 10/334,700, entitled PANEL-TYPE SENSOR/SOURCE ARRAY ASSEMBLY, filed on Dec. 30, 2002, which is herein incorporated by reference.

Figure 16B:
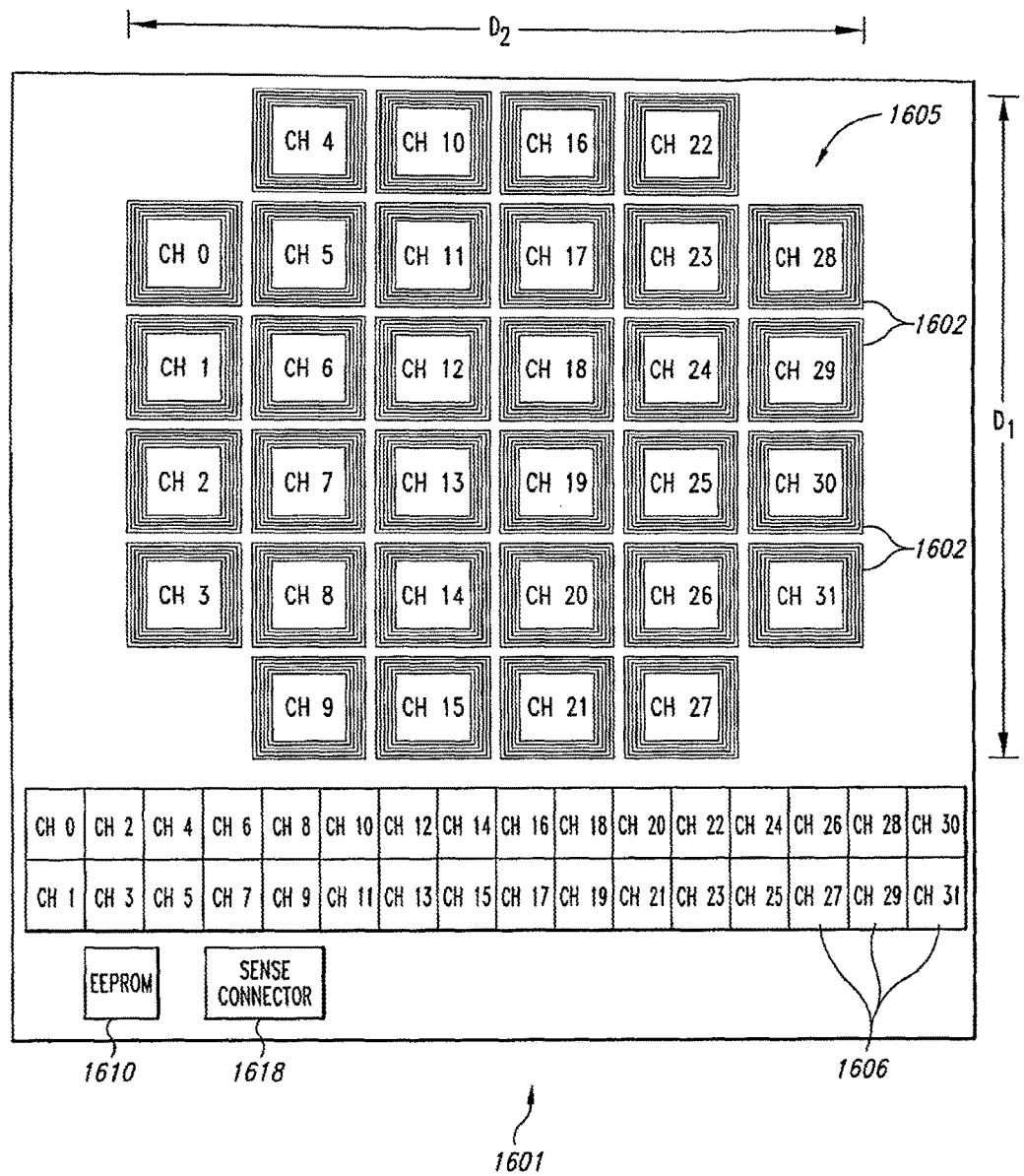
FIG. 16B is a top plan view of a sensing unit for use in the sensor assembly of FIG. 16A.

FIG. 16B further illustrates an embodiment of the sensing unit 1601. In this embodiment, the sensing unit 1601 includes 32 sensor coils 1602; each coil 1602 is associated with a separate output port (channel) 1606 (shown individually as channels "Ch 0" through "Ch 31"). The overall dimension of the panel 1604 can be approximately 40 cm by 54 cm, but the array 1605 has a first dimension D1 of approximately 40 cm and a second dimension D2 of approximately 40 cm. The array 1605 can have other sizes or other configurations (e.g., circular) in alternative embodiments. Additionally, the array 1605 can have more or fewer coils, such as 8-64 coils; the number of coils may moreover be a power of 2.

The coils 1602 may be conductive traces or depositions of copper or another suitably conductive metal formed on the panel 1604. Each coil 1602 has a trace with a width of approximately 0.15 mm and a spacing between adjacent turns within each coil of approximately 0.13 mm. The coils 1602 can have approximately 15 to 90 turns, and in specific applications each coil has approximately 40 turns. Coils with less than 15 turns may not be sensitive enough for some applications, and coils with more than 90 turns may lead to excessive voltage from the source signal during excitation and excessive settling times resulting from the coil's lower self-resonant frequency. In other applications, however, the coils 1602 can have less than 15 turns or more than 90 turns.

As shown in FIG. 16B, the coils 1602 are arranged as square spirals, although other configurations may be employed, such as arrays of circles, interlocking hexagons, triangles, etc. Such square spirals utilize a large percentage of the surface area to improve the signal-to-noise ratio. Square coils also simplify design layout and modeling of the array compared to circular coils; for example, circular coils could waste surface area for linking magnetic flux from the markers 40. The coils 1602 have an inner dimension of approximately 40 mm, and an outer dimension of approximately 62 mm, although other dimensions are possible depending upon applications. Sensitivity may be improved with an inner dimension as close to an outer dimension as possible given manufacturing tolerances. In several embodiments, the coils 1602 are identical to each other or at least configured substantially similarly.

The pitch of the coils 1602 in the array 1605 is a function of at least in part, the minimum distance between the marker and the coil array. In one embodiment, the coils are arranged at a pitch of approximately 67 mm. This specific arrangement is particularly suitable when the markers 40 are positioned approximately 7-27 cm from the sensor assembly 1012. If the markers are closer than 7 cm, then the sensing subsystem may include sensor coils arranged at a smaller pitch. In general, a smaller pitch is desirable when wireless markers are to be sensed at a relatively short distance from the array of coils. The pitch of the coils 1602, for example, is approximately 50%-200% of the minimum distance between the marker and the array.

In general, the size and configuration of the array 1605 and the coils 1602 in the array depend on the frequency range in which they are to operate, the distance from the markers 40 to the array, the signal strength of the markers, and several other factors. Those skilled in the art will readily recognize that other dimensions and configurations may be employed depending, at least in part, on a desired frequency range and distance from the markers to the coils.

The array 1605 is sized to provide a large aperture to measure the magnetic field emitted by the markers. It can be particularly challenging to accurately measure the signal emitted by an implantable marker that wirelessly transmits a marker signal in response to a wirelessly transmitted energy source because the marker signal is much smaller than the source signal and other magnetic fields in a room (e.g., magnetic fields from CRTs, etc.). The size of the array 1605 can be selected to preferentially measure the near field of the marker while mitigating interference from far field sources. In one embodiment, the array 1605 is sized to have a maximum dimension D1 or D2 across the surface of the area occupied by the coils that is approximately 100% to 300% of a predetermined maximum sensing distance that the markers are to be spaced from the plane of the coils. Thus, the size of the array 1605 is determined by identifying the distance that the marker is to be spaced apart from the array to accurately measure the marker signal, and then arrange the coils so that the maximum dimension of the array is approximately 100% to 300% of that distance. The maximum dimension of the array 1605, for example, can be approximately 200% of the sensing distance at which a marker is to be placed from the array 1605. In one specific embodiment, the marker 40 has a sensing distance of 20 cm and the maximum dimension of the array of coils 1602 is between 20 cm and 60 cm, and more specifically 40 cm.

A coil array with a maximum dimension as set forth above is particularly useful because it inherently provides a filter that mitigates interference from far field sources. As such, one aspect of several embodiments of the invention is to size the array based on the signal from the marker so that the array preferentially measures near field sources (i.e., the field generated by the marker) and filters interference from far field sources.

The coils 1602 are electromagnetic field sensors that receive magnetic flux produced by the markers 40 and in turn produce a current signal representing or proportional to an amount or magnitude of a component of the magnetic field through an inner portion or area of each coil. The field component is also perpendicular to the plane of each coil 1602. Each coil represents a separate channel, and thus each coil outputs signals to one of 32 output ports 1606. A preamplifier, described below, may be provided at each output port 1606. Placing preamplifiers (or impedance buffers) close to the coils minimizes capacitive loading on the coils, as described herein. Although not shown, the sensing unit 1601 also includes conductive traces or conductive paths routing signals from each coil 1602 to its corresponding output port 1606 to thereby define a separate channel. The ports in turn are coupled to a connector 1608 formed on the panel 1604 to which an appropriately configured plug and associated cable may be attached.

The sensing unit 1601 may also include an onboard memory or other circuitry, such as shown by electrically erasable programmable read-only memory (EEPROM) 1610. The EEPROM 1610 may store manufacturing information such as a serial number, revision number, date of manufacture, and the like. The EEPROM 1610 may also store per-channel calibration data, as well as a record of run-time. The run-time will give an indication of the total radiation dose to which the array has been exposed, which can alert the system when a replacement sensing subsystem is required.

Although shown in one plane only, additional coils or electromagnetic field sensors may be arranged perpendicular to the panel 1604 to help determine a three-dimensional location of the markers 40. Adding coils or sensors in other dimensions could increase the total energy received from the markers 40, but the complexity of such an array would increase disproportionately. The inventors have found that three-dimensional coordinates of the markers 40 may be found using the planar array shown in FIGS. 16A-B.

Implementing the sensor assembly 1012 may involve several considerations. First, the coils 1602 may not be presented with an ideal open circuit. Instead, they may well be loaded by parasitic capacitance due largely to traces or conductive paths connecting the coils 1602 to the preamplifiers, as well as a damping network (described below) and an input impedance of the preamplifiers (although a low input impedance is preferred). These combined loads result in current flow when the coils 1602 link with a changing magnetic flux. Any one sensor coil 1602, then, links magnetic flux not only from the marker 40, but also from all the other sensor coils as well. These current flows should be accounted for in downstream signal processing.

A second consideration is the capacitive loading on the coils 1602. In general, it is desirable to minimize the capacitive loading on the coils 1602. Capacitive loading forms a resonant circuit with the coils themselves, which leads to excessive voltage overshoot when the excitation source 1010 is energized. Such a voltage overshoot should be limited or attenuated with a damping or "snubbing" network across the coils 1602. A greater capacitive loading requires a lower impedance damping network, which can result in substantial power dissipation and heating in the damping network.

Another consideration is to employ preamplifiers that are low noise. The preamplification can also be radiation tolerant because one application for the sensor assembly 1012 is with radiation therapy systems that use linear accelerators (LINAC). As a result, PNP bipolar transistors and discrete elements may be preferred. Further, a DC coupled circuit may be preferred if good settling times cannot be achieved with an AC circuit or output, particularly if analog to digital converters are unable to handle wide swings in an AC output signal.

Figure 17:
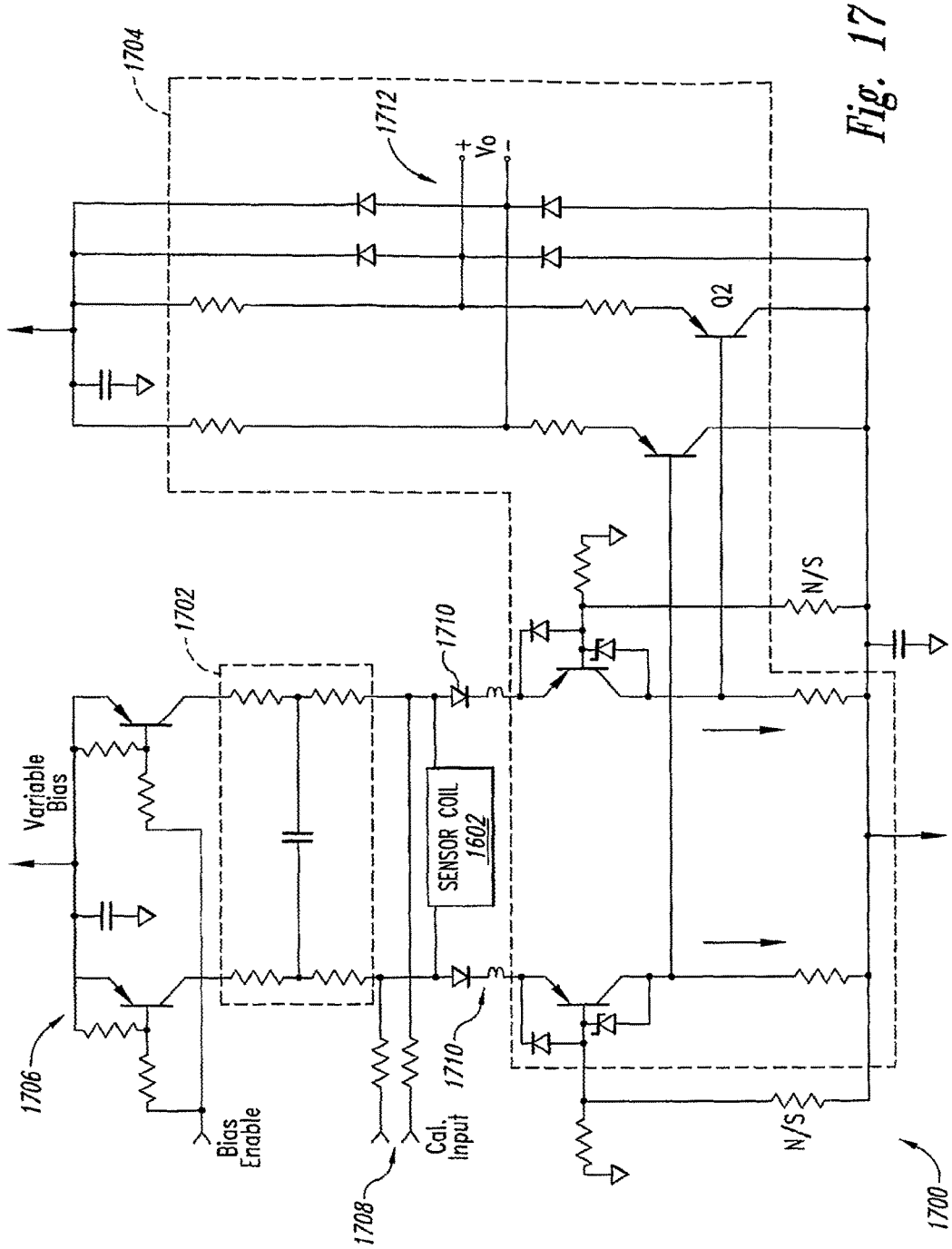
FIG. 17 is a schematic diagram of a preamplifier for use with the sensor assembly of FIG. 16A.

FIG. 17, for example, illustrates an embodiment of a snubbing network 1702 having a differential amplifier 1704. The snubbing network 1702 includes two pairs of series coupled resistors and a capacitor bridging therebetween. A biasing circuit 1706 allows for adjustment of the differential amplifier, while a calibration input 1708 allows both input legs of the differential amplifier to be balanced. The coil 1602 is coupled to an input of the differential amplifier 1704, followed by a pair of high-voltage protection diodes 1710. DC offset may be adjusted by a pair of resistors coupled to bases of the input transistors for the differential amplifier 1704 (shown as having a zero value). Additional protection circuitry is provided, such as ESD protection diodes 1712 at the output, as well as filtering capacitors (shown as having a 10 nF value).

c. Signal Processors and Controllers

The signal processor 1014 and the controller 1016 illustrated in FIG. 10 receive the signals from the sensor assembly 1012 and calculate the absolute positions of the markers 40 within the reference frame. Suitable signal processing systems and algorithms are set forth in U.S. application Ser. Nos. 10/679,801; 10/749,478; 10/750,456; 10/750,164; 10/750,165; 10/749,860; and 10/750,453, all of which are incorporated herein by reference, G. Conclusion The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to target locating and tracking systems, not necessarily the exemplary system generally described above.

The various embodiments described above can be combined to provide further embodiments. All the U.S. patents, U.S. patent application publications, U.S. patent applications, foreign patents, foreign patent applications, and non-patent publications referred to in this specification and/or listed in the Application Data Sheet are incorporated herein by reference, in their entirety. Aspects of the invention can be modified, if necessary, to employ systems, devices, and concepts of the various patents, applications, and publications to provide yet further embodiments of the invention, for example, the markers can be implanted in bone, can be implanted in an intramedullary device, can be affixed to a minimally invasive surgical device and/or can be affixed to a surgical guide.

These and other changes can be made to the invention in light of the above-detailed description. In general, in the following claims, the terms used should not be construed to limit the invention to the specific embodiments disclosed in the specification and the claims, but should be construed to include all target locating and monitoring systems that operate in accordance with the claims to provide apparatus and methods for locating, monitoring, and/or tracking the position of a selected target within a body. Accordingly, the invention is not limited, except as by the appended claims.

We claim:

1. A system for tracking a prosthesis implanted in a human, the system comprising:
   a spinal stabilization device configured to be received in a cavity of the human, wherein the spinal stabilization device includes an inflatable body sized and shaped to be positioned between spinous processes of adjacent superior and inferior vertebrae when the spinal stabilization device is in an expanded state, and wherein the inflatable body includes an aperture through a wall of the inflatable body;
   a magnetic transponder positioned in the aperture of the inflatable body of the spinal stabilization device, wherein a first outer surface of the magnetic transponder protrudes radially from an exterior surface of the inflatable body in a first general direction and defines an exterior outer portion of the spinal stabilization device, wherein a second outer surface of the magnetic transponder protrudes radially from an interior surface of the inflatable body in a second general direction opposite the first general direction and defines an interior portion of the spinal stabilization device, and wherein the transponder has a circuit configured to be energized by a wirelessly transmitted pulsed magnetic field and to wirelessly transmit a pulsed magnetic location signal in response to the pulsed magnetic field; and
   a sensor assembly comprising a support member and a plurality of field sensors carried by the support member configured to sense the pulsed magnetic location signal from the transponder.

2. The system of claim 1 wherein the plurality of field sensors are responsive only to field components of the pulsed magnetic location signal normal to individual field sensors of the plurality of field sensors.

3. The system of claim 1 wherein the field sensors are arranged in an array occupying an area having a maximum dimension of 100% to 300% of a predetermined sensing distance of 20 cm between the transponder and the sensing array.

4. The system of claim 1 wherein the transponder comprises an alternating magnetic circuit having a ferrite core and a coil with a plurality of windings around the ferrite core.

5. The system of claim 1 wherein the inflatable body is a balloon.

6. A system for tracking a prosthesis implanted in a human, the system comprising:
   a spinal stabilization device configured to be received in a cavity of the human, wherein the spinal stabilization device includes an inflatable body sized and shaped to be positioned between spinous processes of adjacent superior and inferior vertebrae when the spinal stabilization device is in an expanded state, wherein the inflatable body has a wall with an outer surface, an inner surface, and a recess extending an intermediate depth into the wall from the outer surface;
   a magnetic transponder positioned in the recess of the inflatable body of the spinal stabilization device, wherein an exterior surface of the magnetic transponder is spaced radially outward from an exterior surface of the inflatable body, and wherein the transponder has a circuit configured to be energized by a wirelessly transmitted pulsed magnetic field and to wirelessly transmit a pulsed magnetic location signal in response to the pulsed magnetic field; and
   a sensor assembly comprising a support member and a plurality of field sensors carried by the support member configured to sense the pulsed magnetic location signal from the transponder.

7. The system of claim 6 wherein the inflatable body is a balloon.

8. The system of claim 7 wherein the inflatable body is made from a compliant material.

9. The system of claim 7 wherein the inflatable body is made from a non-compliant or semi-compliant material.

* * * * *